US012807695B2

(12) United States Patent
Ridinger et al.

(10) Patent No.: US 12,807,695 B2
(45) **Date of Patent: *Nov. 24, 2026**

(54) PLK1 INHIBITOR IN COMBINATION WITH ANTI-ANGIOGENICS FOR TREATING METASTATIC CANCER

(71) Applicant: CARDIFF ONCOLOGY, INC., San Diego, CA (US)

(72) Inventors: Maya Ridinger, San Diego, CA (US); Mark Erlander, San Diego, CA (US)

(73) Assignee: Cardiff Oncology, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/412,419

(22) Filed: Dec. 8, 2025

(65) Prior Publication Data

US 2026/0103509 A1 Apr. 16, 2026

Related U.S. Application Data

(63) Continuation of application No. 19/094,472, filed on Mar. 28, 2025, which is a continuation of application No. 18/751,014, filed on Jun. 21, 2024, now Pat. No. 12,263,173, which is a continuation of application No. PCT/US2023/073865, filed on Sep. 11, 2023.

(60) Provisional application No. 63/515,831, filed on Jul. 26, 2023, provisional application No. 63/405,466, filed on Sep. 11, 2022.

(51) Int. Cl.

| | |
|---|---|
| ***A61K 31/519*** | (2006.01) |
| ***A61K 9/00*** | (2006.01) |
| ***A61K 31/4745*** | (2006.01) |
| ***A61K 31/513*** | (2006.01) |
| ***A61K 35/04*** | (2006.01) |
| ***A61K 39/395*** | (2006.01) |
| ***A61K 45/06*** | (2006.01) |
| ***A61P 35/04*** | (2006.01) |
| ***C07K 16/22*** | (2006.01) |
| *A61K 39/00* | (2006.01) |

(52) U.S. Cl.

CPC ............ *C07K 16/22* (2013.01); *A61K 9/0053* (2013.01); *A61K 31/4745* (2013.01); *A61K 31/513* (2013.01); *A61K 31/519* (2013.01); *A61K 35/04* (2013.01); *A61K 39/3955* (2013.01); *A61K 45/06* (2013.01); *A61P 35/04* (2018.01); *A61K 2039/505* (2013.01); *A61K 2039/545* (2013.01)

(58) Field of Classification Search

CPC .................................................... A61K 31/519

See application file for complete search history.

(56) References Cited

U.S. PATENT DOCUMENTS

| | | | | |
|---|---|---|---|---|
| 8,927,530 | B2 | 1/2015 | Valsasina et al. | |
| 12,144,813 | B2 * | 11/2024 | Ridinger | A61P 35/04 |
| 12,263,173 | B2 * | 4/2025 | Ridinger | A61P 35/04 |
| 2008/0167345 | A1 | 7/2008 | Jones et al. | |
| 2017/0100368 | A1 | 4/2017 | Cox et al. | |

FOREIGN PATENT DOCUMENTS

| | | |
|---|---|---|
| WO | WO2021146322 | 7/2021 |
| WO | WO2021226403 | 11/2021 |

OTHER PUBLICATIONS

Ahn et al. "Phase Ib/II study of the polo-like kinase 1 (PLK1) inhibitor, onvansertib, in combination with FOLFIRI and bevacizumab for second line treatment of KRAS-mutated metastatic colorectal cancer," Annals of Oncology 2020, 31, in 1 page.

Ahn et al. "Phase Ib/II study of the polo-like kinase 1 (PLK1) inhibitor, onvansertib, in combination with FOLFIRI and bevacizumab for second line treatment of KRAS-mutated metastatic colorectal cancer," ESMO Virtual Congress 2020, in 1 page.

Ahn et al., "A phase Ib/II study of the polo-like kinase 1 (PLK1) inhibitor, onvansertib, in combination with FOLFIRI and bevacizumab for second-line treatment of patients with KRAS-mutated metastatic colorectal Cancer (mCRC)," 2021 Gastrointestinal Cancers Symposium, 2021, in 2 pages.

Allegra, Carmen J., et al. "Bevacizumab in stage II-III colon cancer: 5-year update of the National Surgical Adjuvant Breast and Bowel Project C-08 trial." Journal of clinical oncology 31.3 (2013): 359-364.

Amado, Rafael G., et al. "Wild-type KRAS is required for panitumumab efficacy in patients with metastatic colorectal cancer." Journal of clinical oncology 26.10 (2008): 1626-1634.

Antoniotti et al., "TRIBE2 results and toxicity-Authors' reply," The Lancet Oncology 2020, 21(6), e300-e301.

Azam, Faisal, et al. "Performance status assessment by using ECOG (Eastern Cooperative Oncology Group) score for cancer patients by oncology healthcare professionals." Case reports in oncology 12.3 (2020): 728-736.

Barzi et al., "A phase 1 b/2 study of onvansertib (PCM-075) in combination with FOLFIRI and bevacizumab for second line treatment of patients with KRAS-mutated metastatic colorectal cancer (mCRC)." Cancer Res. 2020, 80(16), in 2 pages.

Bennouna et al., "Continuation of bevacizumab after first progression in metastatic colorectal cancer (ML18147): a randomised phase 3 trial," The Lancet Oncology 2013, 14(1), 29-37.

Beretta et al., "FOLFIRI+ bevacizumab as second-line therapy for metastatic colorectal cancer pretreated with oxaliplatin: a pooled analysis of published trials," Medical Oncology 2013, 30, in 8 pages.

Bergh, Jonas, et al. "First-line treatment of advanced breast cancer with sunitinib in combination with docetaxel versus docetaxel alone: results of a prospective, randomized phase III study." Journal of Clinical Oncology 30.9 (2012): 921-929.

(Continued)

*Primary Examiner* — Rei Tsang Shiao

(74) *Attorney, Agent, or Firm* — Dickinson Wright PLLC

(57) ABSTRACT

Provided include methods, compositions and kits for treating metastatic cancer in a subject. The method can comprise administrating a treatment comprising inhibiting angiogenesis and a PLK1 inhibitor (for example, onvansertib) to the subject that has not received prior anti-angiogenic treatment, in a manner sufficient to reduce or inhibit progression of the metastatic cancer.

20 Claims, 12 Drawing Sheets

(56) References Cited

OTHER PUBLICATIONS

Carrato, Alfredo, et al. "Fluorouracil, leucovorin, and irinotecan plus either sunitinib or placebo in metastatic colorectal cancer: a randomized, phase III trial." Journal of Clinical Oncology 31.10 (2013): 1341-1347.
Chiappa, Michela, et al. "Combining PARP inhibition with the polo-like kinase 1 (PLK1) inhibitor onvansertib overcomes PARP inhibitor resistance." Cancer Research. vol. 82. No. 12. 615 Chestnut St, 17th Floor, Philadelphia, PA 19106-4404 USA: Amer Assoc Cancer Research, 2022.
Cremolini et al., "Upfront FOLFOXIRI plus bevacizumab and reintroduction after progression versus mFOLFOX6 plus bevacizumab followed by FOLFIRI plus bevacizumab in the treatment of patients with metastatic colorectal cancer (TRIBE2): a multicentre, open-label, phase 3, randomised, controlled trial," The Lancet Oncology 2020, 21(4), 497-507.
De Gramont, Aimery, et al. "Bevacizumab plus oxaliplatin-based chemotherapy as adjuvant treatment for colon cancer (AVANT): a phase 3 randomised controlled trial." The lancet oncology 13.12 (2012): 1225-1233.
Eisenhauer et al., "New response evaluation criteria in solid tumours: revised RECIST guideline (version 1.1)," European Journal of Cancer 2009, 45(2), 228-247.
Gianni, Luca, et al. "AVEREL: a randomized phase III Trial evaluating bevacizumab in combination with docetaxel and trastuzumab as first-line therapy for HER2-positive locally recurrent/metastatic breast cancer." Journal of clinical oncology 31.14 (2013): 1719-1725.
Giantonio et al., "Bevacizumab in combination with oxaliplatin, fluorouracil, and leucovorin (FOLFOX4) for previously treated metastatic colorectal cancer: results from the Eastern Cooperative Oncology Group Study E3200," Journal of Clinical Oncology 2007, 25(12), 1539-1544.
Giessen et al., "Surrogate endpoints in second-line treatment for mCRC: a systematic literature-based analysis from 23 randomised trials," Acta Oncologica 2015, 54(2), 187-193.
Haibe et al., "Resistance mechanisms to anti-angiogenic therapies in cancer," Frontiers in Oncology 2020, 10, 221.
Hansen et al., "Angiogenesis inhibitors for colorectal cancer. A review of the clinical data," Cancers 2021, 13(5), in 19 pages.
Hecht, J. Randolph, et al. "Randomized, placebo-controlled, phase III study of first-line oxaliplatin- based chemotherapy plus PTK787/ZK 222584, an oral vascular endothelial growth factor receptor inhibitor, in patients with metastatic colorectal adenocarcinoma." Journal of clinical oncology 29.15 (2011): 1997-2003.
Jones et al., "Specific mutations in KRAS codon 12 are associated with worse overall survival in patients with advanced and recurrent colorectal cancer," British Journal of Cancer 2017, 116(7), 923-929.
Karapetis, Christos S., et al. "K-ras mutations and benefit from cetuximab in advanced colorectal cancer." New England Journal of Medicine 359.17 (2008): 1757-1765.
King et al., "Hypoxia and its impact on the tumor microenvironment of gastroesophageal cancers," World Journal of Gastrointestinal Oncology 2021, 13(5), 312-331.
Lenz, et al. "A phase Ib/II study of onvansertib (PCM-075) in combination with FOLFIRI and bevacizumab for second-line treatment of metastatic colorectal cancer in patients with a KRAS mutation." Annals of Oncology 30 (2019), in 1 page.
Lenz et al. "A phase Ib/II study of onvansertib (PCM-075) in combination with FOLFIRI and bevacizumab for second-line treatment of metastatic colorectal cancer in patients with a KRAS mutation." CAS: 2004534872 (2020), in 1 page.
Lenz et al. "A phase Ib/II study of onvansertib (PCM-075) in combination with FOLFIRI and bevacizumab for second-line treatment of metastatic colorectal cancer (mCRC) in patients with a KRAS mutation." Gastrointestinal Cancer Symposium 2020, in 1 page.
Lenz et al., "A phase 1 b/2 trial of the PLK1 inhibitor onvansertib in combination with FOLFIRI-bev in 2L treatment of KRAS-mutated (mKRAS) metastatic colorectal carcinoma (mCRC)," 2022 ASCO Gastrointestinal Cancers Symposium, in 1 page.
Li et al., "Targeting Plk1 to enhance efficacy of olaparib in castration-resistant prostate cancer," Molecular cancer therapeutics 2017, 16(3), 469-479.
Luo et al., "A genome-wide RNAi screen identifies multiple synthetic lethal interactions with the Ras oncogene," Cell 2009, 137(5), 835-848.
Miller, Kathy D., et al. "Randomized phase III trial of capecitabine compared with bevacizumab plus capecitabine in patients with previously treated metastatic breast cancer." Journal of clinical oncology 23.4 (2005): 792-799.
Moriwaki et al., "Bevacizumab in combination with irinotecan, 5-fluorouracil, and leucovorin (FOLFIRI) in patients with metastatic colorectal cancer who were previously treated with oxaliplatin-containing regimens: a multicenter observational cohort study (TCTG 2nd-BV study)," Medical Oncology 2012, 29, 2842-2848.
Mross, K., et al. "A randomised phase II trial of the Polo-like kinase inhibitor BI 2536 in chemo-naïve patients with unresectable exocrine adenocarcinoma of the pancreas—a study within the Central European Society Anticancer Drug Research (CESAR) collaborative network." British journal of cancer 107.2 (2012): 280-286.
Nie, Zhe, et al. "Discovery of TAK-960: an orally available small molecule inhibitor of polo-like kinase 1 (PLK1)." Bioorganic & medicinal chemistry letters 23.12 (2013): 3662-3666.
Oken, et al., "Toxicity and response criteria of the Eastern Cooperative Oncology Group," American Journal of Clinical Oncology 1982, 5(6), 649-656.
Patelli, G., et al. "Strategies to tackle RAS-mutated metastatic colorectal cancer." ESMO open 6.3 (2021): 100156.
Popravka et al., "HIF-1 as a Marker of Age-Related Diseases Associated with Tissue Hypoxia," Biology Bulletin Reviews 2018, 8, 497-508.
Rocchetti et al., "Predictive pharmacokinetic-pharmacodynamic modeling of tumor growth after administration of an anti-angiogenic agent, bevacizumab, as single-agent and combination therapy in tumor xenografts," Cancer Chemother Pharmacol. 2013, 71(5), 1147-1157.
Sharma, Manish R. "Expanded access program of the PLK1 inhibitor onvansertib for treatment of patients with KRAS-mutant metastatic colorectal cancer" Jul. 1, 2021 Cancer Research, 81(13), 425.
Tabernero et al., "Aflibercept versus placebo in combination with fluorouracil, leucovorin and irinotecan in the treatment of previously treated metastatic colorectal cancer: prespecified subgroup analyses from the VELOUR trial," European Journal of Cancer 2014, 50(2), 320-331.
Tabernero et al., "Ramucirumab versus placebo in combination with second-line FOLFIRI in patients with metastatic colorectal carcinoma that progressed during or after first-line therapy with bevacizumab, oxaliplatin, and a fluoropyrimidine (RAISE): a randomized, double-blind, multicenter, phase 3 study," The Lancet Oncology 2015, 16(5), 499-508.
Ternyila, Danielle "Onvansertib Receives FDA Fast Track Designation in KRAS+ mCRC" Targeted Oncology, May 28, 2020, Available at: https://www.targetedonccom/view/onvansertib-receives-fda-fast-track-designation-in-kras-mcrc, Last accessed Aug. 27, 2024, in 3 Pages.
Therasse et al., "New guidelines to evaluate the response to treatment in solid tumors," Journal of the National Cancer Institute 2000, 92(3), 205-216.
Tie et al., "Circulating tumor DNA as an early marker of therapeutic response in patients with metastatic colorectal cancer," Annals of Oncology 2015, 26(8), 1715-1722.
Tol, Jolien, et al. "Chemotherapy, bevacizumab, and cetuximab in metastatic colorectal cancer." New England Journal of Medicine 360.6 (2009): 563-572.
Tucker, N. Onvansertib Plus FOLFIRI/Bevacizumab Generates Meaningful Responses in KRAS-Mutant mCRC. Gastrointestinal Cancers Symposium (ASCO GI), Jan. 22, 2022.
U.S. National Library of Medicine, "Onvansertib in Combination With FOLFIRI and Bevacizumab for Second Line Treatment of Metastatic Colorectal Cancer Patients With a Kras Mutation,"

(56) References Cited

OTHER PUBLICATIONS https://www.clinicaltrials.gov/study/NCT03829410?tab=history&a=1#version-content-panel, Feb. 4, 2019, Last Accessed Dec. 20, 2024, in 16 pages.
U.S. National Library of Medicine, "Onvansertib in Combination With FOLFIRI and Bevacizumab for Second Line Treatment of Metastatic Colorectal Cancer Patients With a Kras Mutation," https://clinicaltrials.gov/study/NCT03829410?tab=history&a=13, Apr. 30, 2021, Last Accessed Dec. 18, 2023, in 9 pages.
U.S. National Library of Medicine, "Onvansertib in Combination With FOLFIRI and Bevacizumab for Second Line Treatment of Metastatic Colorectal Cancer Patients With a Kras Mutation," https://clinicaltrials.gov/study/NCT03829410?tab=history&a=13#version-content-panel, Apr. 30, 2021, Last accessed Aug. 23, 2024, in 17 Pages.
U.S. National Library of Medicine, "Onvansertib in Combination With FOLFIRI and Bevacizumab for Second Line Treatment of Metastatic Colorectal Cancer Patients With a Kras Mutation," ClinicalTrials.gov 2023, in 10 pages. https://www.clinicaltrials.gov/study/NCT03829410.
U.S. National Library of Medicine, "Onvansertib in Combination With FOLFIRI and Bevacizumab for Second Line Treatment of Metastatic Colorectal Cancer Patients With a Kras Mutation," ClinicalTrials.gov 2024, in 16 pages. https://www.clinicaltrials.gov/study/NCT03829410.
Van Cutsem et al., "Addition of aflibercept to fluorouracil, leucovorin, and irinotecan improves survival in a phase III randomized trial in patients with metastatic colorectal cancer previously treated with an oxaliplatin-based regimen," J Clin Oncol 2012, 30(28), 3499-3506.
Van Cutsem et al., "Impact of prior bevacizumab treatment on VEGF-A and PIGF levels and outcome following second-line aflibercept treatment: biomarker post hoc analysis of the VELOUR trial," Clinical Cancer Research 2020, 26(3), 717-725.
Weichert et al., "Polo-like kinase 1 expression is a prognostic factor in human colon cancer," World Journal of Gastroenterology 2005, 11(36), 5644-5650.
Welti, Jonathan C., et al. "Contrasting effects of sunitinib within in vivo models of metastasis." Angiogenesis 15 (2012): 623-641.

* cited by examiner

Best Radiographic Response and Duration of Response* – 66 evaluable patients (as of June 16, 2023)

| | All patients | Bev naive | Bev exposed |
|---|---|---|---|
| N | 66 | 15 | 51 |
| ORR | 29% | 73% | 16% |
| 95% CI | (18-41%) | (45-92%) | (7-29%) |
| mDOR | 12.0mo | 13.0mo | 8.9mo |
| 95% CI | (8.9, –) | (12.0, –) | (3.9, –) |
| Disease Control Rate | 92% | 100% | 90% |

Historical controls**

| | | | |
|---|---|---|---|
| ORR | | 23-26% | 5-13% |

*FIG. 4A*

PLK1 INHIBITOR IN COMBINATION WITH ANTI-ANGIOGENICS FOR TREATING METASTATIC CANCER

BACKGROUND

Field

The present disclosure relates generally to the field of treatment for cancer.

Description of the Related Art

The Polo-like kinase 1 (PLK1) is a serine/threonine kinase and the most well characterized member of this family of 5 closely related regulatory proteins. PLK-1 is a master regulator of mitosis via its control of the entry and progression of cells into and through mitosis. PLK1 performs several important functions throughout mitotic (M) phase of the cell cycle, including the regulation of centrosome maturation and spindle assembly, the removal of cohesins from chromosome arms, the inactivation of anaphase-promoting complex/cyclosome (APC/C) inhibitors, and the regulation of mitotic exit and cytokinesis. PLK1 plays a key role in centrosome functions and the assembly of bipolar spindles. PLK1 controls kinetochore interactions with the spindle microtubules that is required for successful separation and segregation chromatids to the appropriate mother and daughter cells. PLK1 also acts as a negative regulator of p53 family members leading to ubiquitination and subsequent degradation of p53/TP53, inhibition of the p73/TP73 mediated pro-apoptotic functions and phosphorylation/degradation of bora, a cofactor of Aurora kinase A. During the various stages of mitosis PLK1 localizes to the centrosomes, kinetochores and central spindle. PLK1 is aberrantly overexpressed in a variety of human cancers and is correlated with cellular proliferation and poor prognosis.

The most advanced stage of cancer is stage IV, which is defined by the cancer spreading to distant parts of the body from where the cancer first originated (e.g., metastasis). Angiogenesis is necessary for metastasis to occur and several anti-angiogenics have been approved for use in humans to treat metastatic cancers. However, according to the Centers for Disease Control and Prevention, about one in every five deaths in the United states is still due to cancer. There is a need for more effective treatments for advanced (e.g., metastatic) cancers.

SUMMARY

Disclosed herein include methods of treating cancer, including a metastatic cancer. The method for treating cancer can, in some embodiments, comprise administering a PLK1 inhibitor and an anti-angiogenics to a subject with a metastatic cancer, thereby reducing or inhibiting progression of the metastatic cancer, where the subject has not received any prior treatment comprising inhibiting angiogenesis. The method for treating cancer can, in some embodiments, comprises administering a PLK1 inhibitor and an anti-angiogenics to the subject, thereby reducing or inhibiting progression of the metastatic cancer, wherein the subject has not received any prior cancer treatment or the subject has not received any prior treatment comprising inhibiting angiogenesis. The method for treating cancer can, in some embodiments, comprise administering a PLK1 inhibitor and an anti-angiogenics to the subject, thereby reducing or inhibiting progression of the metastatic cancer, where the subject is known to have not received any prior cancer treatment or the subject is known to have not received any prior treatment comprising inhibiting angiogenesis. The method for treating cancer can, in some embodiments, comprises identifying a subject having a metastatic cancer and has not received any prior cancer treatment; and administering a PLK1 inhibitor and an anti-angiogenics to the subject, thereby reducing or inhibiting progression of the metastatic cancer. The method, in some embodiments, comprises: identifying a subject having a metastatic cancer and has not received any prior treatment comprising inhibiting angiogenesis; and administering a PLK1 inhibitor and an anti-angiogenics to the subject, thereby reducing or inhibiting progression of the metastatic cancer.

In some embodiments, the method comprises administering the subject with a chemotherapy, the PLK1 inhibitor and the anti-angiogenics. In some embodiments, the subject has not been received prior chemotherapy treatment. In some embodiments, the subject has not been received prior chemotherapy treatment for the metastatic cancer. The chemotherapy can comprise a treatment using FOLFIRI, abiraterone, FOLFOX, an anti-EGFR agent, a KRAS directed inhibitor, gemcitabine, abraxane, nanoliposomal irinotecan, 5-FU, FOLFIRINOX, FOLFOXIRI, or a combination thereof.

In some embodiments, administering the PLK1 inhibitor and the anti-angiogenics synergistically reduces or inhibits progression of the metastatic cancer relative to the PLK1 inhibitor treatment alone, the anti-angiogenics treatment alone, and/or the additive effect of the PLK1 inhibitor treatment alone and the anti-angiogenics treatment alone. In some embodiments, administering the PLK1 inhibitor and the anti-angiogenics improves one or more therapeutic effects in the subject relative to a control or a baseline. In some embodiments, administering the PLK1 inhibitor and the anti-angiogenics reduces oncogenic allelic burden in the subject relative to subjects who have received prior treatment comprising inhibiting angiogenesis.

Also disclosed herein includes methods of improving objective response rate (ORR), progression free survival (PFS), or both in treating a metastatic cancer. The method, in some embodiments, comprises administering a PLK1 inhibitor and an anti-angiogenics to subjects suffering from a metastatic cancer, thereby improving the ORR and/or the PFS of the subjects, wherein the subjects have not received any prior cancer treatment or the subjects have not received any prior treatment comprising inhibiting angiogenesis. The method, in some embodiments, comprises administering a PLK1 inhibitor and an anti-angiogenics to subjects suffering from a metastatic cancer, thereby improving the ORR and/or the PFS of the subjects, wherein the subjects are known to have not received any prior cancer treatment or the subjects are known to have not received any prior treatment comprising inhibiting angiogenesis. In some embodiments, the method comprises identifying the subjects have the metastatic cancer and have not received any prior cancer treatment. In some embodiments, the method comprises identifying the subjects have the metastatic cancer and have not received any prior treatment comprising inhibiting angiogenesis. In some embodiments, administering the PLK1 inhibitor and the anti-angiogenics synergistically improves the ORR and/or the PFS of the subjects relative to the PLK1 inhibitor treatment alone, the anti-angiogenics treatment alone, and/or the additive effect of the PLK1 inhibitor treatment alone and the anti-angiogenics treatment alone. In some embodiments, administering the PLK1 inhibitor and the anti-angiogenics improves one or more therapeutic effects in the subjects relative to a control or a baseline; and optionally the one or more therapeutic effects comprise size of a tumor derived from the metastatic cancer, objective response rate (ORR), duration of response, time to response, progression free survival (PFS), overall survival (OS), disease control rate (DCR), oncogenic allelic burden, or a combination thereof. In some embodiments, administering the PLK1 inhibitor and the anti-angiogenics improves the ORR in the subjects, improves PFS in the subjects, improves OS in the subjects, improves DCR in the subjects, reduces oncogenic allelic burden in the subjects, or a combination thereof, relative to subjects who have received prior treatment comprising inhibiting angiogenesis. In some embodiments, administering the PLK1 inhibitor and the anti-angiogenics improves the ORR, the PFS or both in the subjects by at least 50% relative to subjects who have received prior treatment comprising inhibiting angiogenesis. In some embodiments, administering the PLK1 inhibitor and the anti-angiogenics to the subjects results in an ORR difference of 50%, 55%, 65%, 70%, 75%, or more, or a number or a range between any two of these values in the subjects. In some embodiments, administering the PLK1 inhibitor and the anti-angiogenics to the subjects results in an mPFS of 11 months, 12 months, 13 months, 14 months, 15 months, 16 months, 17 months, 18 months, 19 months, 20 months, or more, or a number or a range between any two of these values in the subjects. As described herein, administering the PLK1 inhibitor and the anti-angiogenics to the subjects can comprises administering the PLK1 inhibitor, the anti-angiogenics and one or more anti-cancer therapeutics or therapies (e.g., one or more chemotherapies) to the subject.

Non-limiting examples of the metastatic cancer include metastatic colorectal cancer, metastatic bladder cancer, metastatic breast cancer, metastatic kidney cancer, metastatic lung cancer, metastatic ovarian cancer, metastatic pancreatic cancer, metastatic prostate cancer, metastatic stomach cancer, metastatic thyroid cancer, metastatic uterine cancer, metastatic renal cancer, metastatic cervical cancer, metastatic recurrent glioblastoma, or a combination thereof.

In some embodiments, the PLK1 inhibitor is selective and/or specific for PLK1. In some embodiments, the PLK1 inhibitor is onvansertib, BI2536, Volasertib (BI 6727), GSK461364, AZD1775, CYC140, HMN-176, HMN-214, rigosertib (ON-01910), MLN0905, TKM-080301, TAK-960, or Ro3280. In some embodiments, the subject has not received any prior treatment comprising administration of an angiogenesis inhibitor, and optionally wherein the angiogenesis inhibitor is the same as the anti-angiogenics. In some embodiments, the anti-angiogenics is bevacizumab. In some embodiments, the angiogenesis inhibitor is bevacizumab.

The PLK1 inhibitor and the anti-angiogenics can be administered simultaneously or sequentially. In some embodiments, the PLK1 inhibitor is administered prior to the administration of the anti-angiogenics, and optionally wherein the PLK1 inhibitor is administered prior to the administration of the anti-angiogenics every day on which the subject is administered with the PLK1 inhibitor and the anti-angiogenics. In some embodiments, the PLK1 inhibitor is administered about 30 minutes to about 5 hours prior to the administration of the anti-angiogenics on a given day. In some embodiments, the administration of the PLK1 inhibitor is oral administration, and the administration of the anti-angiogenics is intravenous administration or oral administration. In some embodiments, the anti-angiogenics and the PLK1 inhibitor are each administered to the subject in a cycle of at least twice or at least five times within a week. In some embodiments, the anti-angiogenics, the PLK1 inhibitor, or both are administered in a cycle of at least 7 days; optionally each cycle of treatment is at least about 21 days; and further optionally each cycle of treatment is from about 21 days to about 28 days.

In some embodiments, the PLK1 inhibitor is administered on at least four days in the cycle. In some embodiments, the PLK1 inhibitor is not administered on at least one day in the cycle. In some embodiments, the anti-angiogenics is administered daily, weekly, bi-weekly, every three weeks, every four weeks, or every month. In some embodiments, the subject undergoes at least two cycles of the administration of the anti-angiogenics and the PLK1 inhibitor. In some embodiments, the anti-angiogenics is bevacizumab and the PLK1 inhibitor is onvansertib. Onvansertib can be administered at, for example, 12 $mg/m^2$-90 $mg/m^2$. Bevacizumab can be administered at, for example, about 1 mg/kg-20 mg/kg; optionally wherein bevacizumab is administered at about 5 mg/kg, about 7.5 mg/kg, about 10 mg/kg, or about 15 mg/kg.

In some embodiments, the subject has received at least one prior cancer treatment, and optionally wherein the prior treatment does not comprise the use of an anti-angiogenics, a PLK1 inhibitor, or both. In some embodiments, the subject or the subjects had a prior remission for cancer. The prior remission can be complete remission (CR) or partial remission (PR).

In some embodiments, the method further comprises one or more of (1) determining cancer status of the subject or the subjects, (2) determining responsiveness of the subject or the subjects to a PLK1 inhibitor treatment, and (3) administering to the subject or the subjects one or more cancer therapeutics or therapies. The subject or the subjects can be human.

In some embodiments, reducing or inhibiting progression of the cancer comprises inhibition of growth of one or more tumors in the subject or the subjects and/or reducing the number of cancer cells detected in the subject or the subjects by at least about 25%, 30%, 40%, 50%, 60%, or 70% relative to an untreated subject. In some embodiments, reducing or inhibiting progression of the cancer comprises inhibition of growth of one or more tumors in the subject or the subjects and/or reducing the number of cancer cells detected in the subject or the subjects by at least about 25%, 30%, 40%, 50%, 60%, or 70% relative to the subject or the subjects prior to administration of the PLK1 inhibitor and the anti-angiogenics. In some embodiments, the growth of at least one of the one or more tumors in the subject or the subjects is reduced by at least about 25%, 30%, 40%, 50%, 60%, or 70% following one or more cycles of treatment. In some embodiments, the size/volume of at least one of the one or more tumors in the subject or the subjects is reduced by at least about 25%, 30%, 40%, 50%, 60%, or 70% following one or more cycles of treatment.

In some embodiments, the one or more cancer therapeutics or therapies comprise FOLFIRI, abiraterone, FOLFOX, an anti-EGFR agent, a KRAS directed inhibitor, gemcitabine, abraxane, nanoliposomal irinotecan, 5-FU, or a combination thereof; wherein the anti-EGFR agents is optionally cetuximab, and KRAS directed inhibitor is optionally a G12C inhibitor, a G12D inhibitor, or a combination thereof. In some embodiments, determining the responsiveness of the subject or the subjects comprises determining if the subject is a responder of the treatment, if the subject or the subjects is or is going to be in complete recovery (CR), or if the subject or the subjects is or is going to be in partial remission (PR). In some embodiments, determining the responsiveness of the subjects comprises determining objective response rate (ORR), duration of response, time to response, progression free survival (PFS), overall survival (OS), disease control rate (DCR), oncogenic allelic burden, or a combination thereof of the subjects. In some embodiments, determining the responsiveness of the subject or the subjects comprises determining if the subject or the subjects have a partial response to the treatment, if the subject have a complete response to the treatment, if the subject has a stable disease (SD) status, or if the subject has a progressive disease (PD) status.

Also disclosed herein incudes kits. The kit, in some embodiments, comprises a PLK1 inhibitor; and a manual providing instructions for administrating the PLK1 inhibitor with an anti-angiogenics to a subject having a metastatic cancer, wherein the subject has not received any prior cancer treatment or the subject has not received any prior treatment comprising inhibiting angiogenesis. The kit, in some embodiments, comprises a PLK1 inhibitor; and a manual providing instructions for administrating the PLK1 inhibitor with an anti-angiogenics to a subject having a metastatic cancer, wherein the subject is known to have not received any prior cancer treatment or the subject is known to have not received any prior treatment comprising inhibiting angiogenesis.

In some embodiments, the instructions comprise instructions for administrating the PLK1 inhibitor and the anti-angiogenics simultaneously. In some embodiments, the instructions comprise instructions for administrating the PLK1 inhibitor and the anti-angiogenics sequentially. In some embodiments, the instructions comprise (1) instructions for administering of the PLK1 inhibitor orally, (2) instructions for administrating the anti-angiogenics orally, (3) instructions for administrating the anti-angiogenics intravenously, or any combination thereof. In some embodiments, the instructions comprise instructions wherein the subject has not received any prior treatment comprising administration of an angiogenesis inhibitor, and optionally wherein the angiogenesis inhibitor is the same as the anti-angiogenics. In some embodiments, the instructions comprise instructions for administering each of the anti-angiogenics and the PLK1 inhibitor to the subject in a cycle of at least twice or at least five times within a week. In some embodiments, the instructions comprise instructions for administering the anti-angiogenics, the PLK1 inhibitor, or both are in a cycle of at least 7 days; and optionally wherein each cycle of treatment is at least about 21 days, and further optionally each cycle of treatment is from about 21 days to about 28 days. In some embodiments, the instructions comprise instructions for administering the PLK1 inhibitor on at least four days in the cycle. In some embodiments, the instructions comprise instructions for not administering the PLK1 inhibitor on at least one day in the cycle.

In some embodiments, the instructions comprise instructions for administrating the anti-angiogenics daily, weekly, bi-weekly, every three weeks, every four weeks, or monthly. In some embodiments, the instructions comprise instructions for administrating the anti-angiogenics and the PLK1 inhibitor for at least two cycles. The anti-angiogenics can be bevacizumab. The PLK1 inhibitor can be onvansertib. In some embodiments, the instructions comprise instructions for administering onvansertib at 12 $mg/m^2$-90 $mg/m^2$. In some embodiments, the kit further comprises the anti-angiogenic.

BRIEF DESCRIPTION OF THE DRAWINGS

FIGS. 4A-4B show best radiographic response and duration of response for 66 evaluable patients (as of Jun. 16, 2023). *Radiographic response determined per RECIST 1.1. Waterfall plot and table reflect interim data as of Jun. 16, 2023 from an ongoing trial and unlocked database. Patients 02-008 and 07-029 were categorized as bev naïve in the Jul. 25, 2022 data, but are now determined to have been bev exposed. mDOR CI: "-" means not reached. After external review of the tumor measurements completed May 12, 2023, it was determined that patients 02-028 and 04-038 were confirmed PRs.

DETAILED DESCRIPTION

Figure 1:
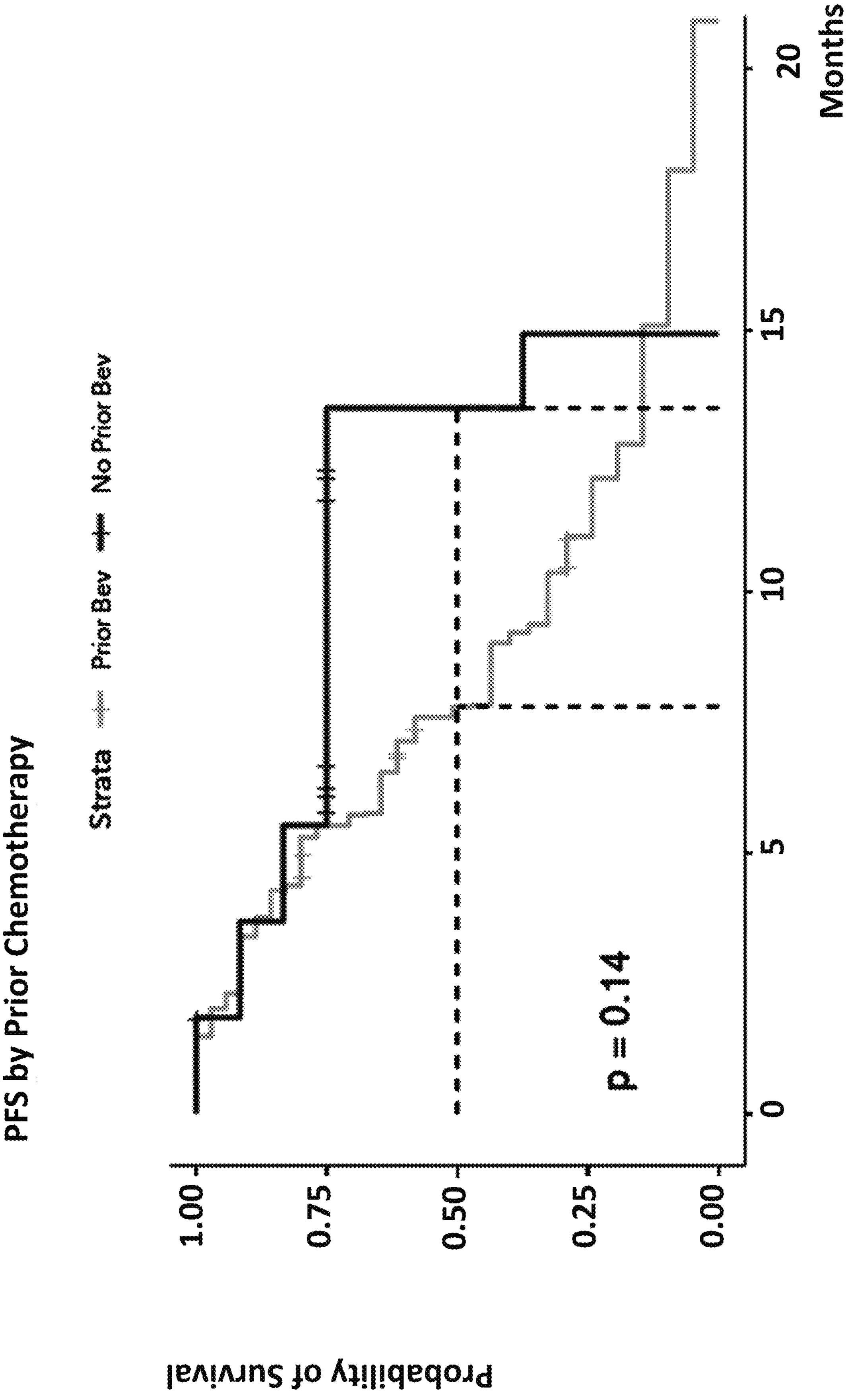
FIG. 1 depicts an exemplary Kaplan-Meir survival curve of cancer patients treated using the methods and compositions provided herein, with or without prior anti-angiogenics treatments.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein include methods of treating cancer. In some embodiments, the method comprises: administering a PLK1 inhibitor and an anti-angiogenics to a subject with a metastatic cancer, thereby reducing or inhibiting progression of the metastatic cancer, wherein the subject has not received any prior treatment comprising inhibiting angiogenesis or wherein the subject has not received any cancer treatment (e.g., a treatment for the metastatic cancer). The method can, in some embodiments, comprise administering a PLK1 inhibitor and an anti-angiogenics to the subject, thereby reducing or inhibiting progression of the metastatic cancer, where the subject is known to have not received any prior cancer treatment or the subject is known to have not received any prior treatment comprising inhibiting angiogenesis. The method for treating cancer can, in some embodiments, comprises identifying a subject having a metastatic cancer and has not received any prior cancer treatment; and administering a PLK1 inhibitor and an anti-angiogenics to the subject, thereby reducing or inhibiting progression of the metastatic cancer. The method, in some embodiments, comprises: identifying a subject having a metastatic cancer and has not received any prior treatment comprising inhibiting angiogenesis; and administering a PLK1 inhibitor and an anti-angiogenics to the subject, thereby reducing or inhibiting progression of the metastatic cancer. Any of the methods disclosed herein can be used in a first line treatment for the metastatic cancer, a second line treatment for the metastatic cancer, or both. It is known that for receiving a second line cancer treatment, a subject would have received at least one prior cancer treatment which had failed, stopped working, and/or had side effects that were not tolerated. As disclosed herein, in some embodiments, the subject being treated by the method disclosed herein has failed a treatment or is intolerant of the treatment (e.g., a chemotherapy treatment, including an oxaliplatin-based chemotherapy). In some embodiment, the chemotherapy treatment is a chemotherapy of fluoropyrimidine and oxaliplatin.

Disclosed herein include methods of improving objective response rate (ORR), progression free survival (PFS), or both in treating a metastatic cancer. The method, in some embodiments, comprises administering a PLK1 inhibitor and an anti-angiogenics to subjects suffering from a metastatic cancer, thereby improving the ORR and/or the PFS of the subjects, wherein the subjects have not received any prior cancer treatment (e.g., a treatment for the metastatic cancer) or the subjects have not received any prior treatment comprising inhibiting angiogenesis. The method, in some embodiments, comprises administering a PLK1 inhibitor and an anti-angiogenics to subjects suffering from a metastatic cancer, thereby improving the ORR and/or the PFS of the subjects, wherein the subjects are known to have not received any prior cancer treatment (e.g., a treatment for the metastatic cancer) or the subjects are known to have not received any prior treatment comprising inhibiting angiogenesis. The methods can be used in a first-line treatment for the metastatic cancer, a second-line treatment for the metastatic cancer, or both.

Disclosed herein include compositions and kits for treating cancer. In some embodiments, the kit comprises: a PLK1 inhibitor; and a manual providing instructions for administrating the PLK1 inhibitor with an anti-angiogenics to a subject for treating a metastatic cancer, wherein the subject has not received any prior treatment comprising inhibiting angiogenesis or wherein the subject has not received any cancer treatment (e.g., a treatment for the metastatic cancer).

DEFINITIONS

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, a "subject" refers to an animal that is the object of treatment, observation or experiment. "Animals" include cold- and warm-blooded vertebrates and invertebrates such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional, such as a Medical Doctor or a Doctor of Veterinary Medicine, to attempt to cure, or at least ameliorate the effects of, a particular disease or disorder or to prevent the disease or disorder from occurring in the first place. The patient can be an animal. In some embodiments, the patient is a mammal. In some embodiments, the patient is a human.

As used herein, "administration" or "administering" refers to a method of giving a dosage of a pharmaceutically active ingredient to a vertebrate.

As used herein, a "dosage" refers to the combined amount of the active ingredients (e.g., PLK1 inhibitor (e.g., onvansertib) or anti-angiogenics (e.g., bevacizumab)).

As used herein, a "unit dosage" refers to an amount of therapeutic agent administered to a patient in a single dose.

As used herein, the term "daily dose" or "daily dosage" refers to a total amount of a pharmaceutical composition or a therapeutic agent that is to be taken within 24 hours.

As used herein, the term "delivery" refers to approaches, formulations, technologies, and systems for transporting a pharmaceutical composition or a therapeutic agent into the body of a patient as needed to safely achieve its desired therapeutic effect. In some embodiments, an effective amount of the composition or agent is formulated for delivery into the blood stream of a patient.

As used herein, the term "formulated" or "formulation" refers to the process in which different chemical substances, including one or more pharmaceutically active ingredients, are combined to produce a dosage form. In some embodiments, two or more pharmaceutically active ingredients can be co-formulated into a single dosage form or combined dosage unit, or formulated separately and subsequently combined into a combined dosage unit. A sustained release formulation is a formulation which is designed to slowly release a therapeutic agent in the body over an extended period of time, whereas an immediate release formulation is a formulation which is designed to quickly release a therapeutic agent in the body over a shortened period of time.

As used herein, the term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile.

As used herein, the term "pharmaceutically acceptable carrier" refers to pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body, or to deliver an agent to a diseased tissue or a tissue adjacent to the diseased tissue. Carriers or excipients can be used to produce compositions. The carriers or excipients can be chosen to facilitate administration of a drug or pro-drug. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

As used herein, the term "pharmaceutically acceptable salt" refers to any acid or base addition salt whose counter-ions are non-toxic to the patient in pharmaceutical doses of the salts. A host of pharmaceutically acceptable salts are well known in the pharmaceutical field. If pharmaceutically acceptable salts of the compounds of this disclosure are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate, undecanoate, hydrohalides (e.g., hydrochlorides and hydrobromides), sulphates, phosphates, nitrates, sulphamates, malonates, salicylates, methylene-bis-b-hydroxynaphthoates, gentisates, isethionates, di-p-toluoyltartrates, ethanesulphonates, cyclohexylsulphamates, quinates, and the like. Pharmaceutically acceptable base addition salts include, without limitation, those derived from alkali or alkaline earth metal bases or conventional organic bases, such as triethylamine, pyridine, piperidine, morpholine, N-methylmorpholine, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

As used herein, each of the terms "partial response," "partial remission," or "PR" refers to the amelioration of a cancerous state, as measured by, for example, tumor size and/or cancer marker levels, in response to a treatment. In some embodiments, a "partial response" means that a tumor or tumor-indicating blood marker has decreased in size or level by about 50% in response to a treatment. The treatment can be any treatment directed against cancer, including but not limited to, chemotherapy, radiation therapy, hormone therapy, surgery, cell or bone Marrow transplantation, and immunotherapy. The size of a tumor can be detected by clinical or by radiological means. Tumor-indicating markers can be detected by means well known to those of skill, e.g., ELISA or other antibody-based tests.

As used herein, each of the terms "complete response," "complete remission," "complete recovery," or "CR" refers to a cancerous state, as measured by, for example, tumor size and/or cancer marker levels, has disappeared following a treatment, including but are not limited to, chemotherapy, radiation therapy, hormone therapy, surgery, cell or bone marrow transplantation, and immunotherapy. The presence of a tumor can be detected by clinical or by radiological means. Tumor-indicating markers can be detected by means well known to those of skill, e.g., ELISA or other antibody-based tests. However, a "complete response" does not necessarily indicate that the cancer has been cured. A complete response may be followed by a relapse. A complete response of a target lesion includes disappearance of all target lesions and any pathological lymph nodes (whether target or non-target) having reduction in short axis to <10 mm. A complete response of a non-target lesion includes disappearance of all non-target lesions and normalization of tumor marker level (all lymph nodes must be non-pathological in size (<10 mm short axis)). If tumor markers are initially above the upper normal limit, they need to normalize for a patient to be considered in complete clinical response of a nontarget lesion. The duration of overall CR is measured from the time measurement criteria are first met for CR until the first date that progressive disease is objectively documented, or death due to any cause. Participants without events reported are censored at the last disease evaluation.

As used herein, the term "stable disease" or "SD" means neither sufficient shrinkage to qualify for PR nor sufficient increase to qualify for progressive disease (PD), taking as reference the smallest sum diameters while on study. Duration of stable disease is measured from the start of the treatment until the criteria for progression are met, taking as reference the smallest measurements recorded since the treatment started, including the baseline measurements.

As used herein, the term "progressive disease" or "PD" when refers to a target lesion means at least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression). When progressive disease or PD refers to a non-target lesion, it means the appearance of one or more new lesions and/or unequivocal progression of existing non-target lesions. Unequivocal progression should not normally trump target lesion status. It must be representative of overall disease status change, not a single lesion increase.

As used herein, the term "overall survival" or "OS" means the time from randomization (or registration) to death due to any cause. Participants survived are censored on date last known alive.

As used herein, the term "progression-free survival" or "PFS" means the time from randomization (or registration) to the earlier of progression or death due to any cause. Participants alive without disease progression are censored on date of last disease evaluation.

As used herein, the term "best overall response" means the best response recorded from the start of the treatment until disease progression/recurrence (taking as reference for progressive disease the smallest measurements recorded since the treatment started). The patient's best response assignment depends on the achievement of both measurement and confirmation criteria. The duration of an overall response is measured from the time measurement criteria are met for CR or PR (whichever is first recorded) until the first date that recurrent or progressive disease is objectively documented (taking as reference for progressive disease the smallest measurements recorded since the treatment started, or death due to any cause. Participants without events reported are censored at the last disease evaluation).

As used herein, the term "hydrate" refers to a complex formed by combination of water molecules with molecules or ions of the solute. As used herein, the term "solvate" refers to a complex formed by combination of solvent molecules with molecules or ions of the solute. The solvent can be an organic compound, an inorganic compound, or a mixture of both. Solvate is meant to include hydrate, hemi-hydrate, channel hydrate etc. Some examples of solvents include, but are not limited to, methanol, N,N-dimethylformamide, tetrahydrofuran, dimethylsulfoxide, and water.

As used herein, "therapeutically effective amount" or "pharmaceutically effective amount" refers to an amount of therapeutic agent, which has a therapeutic effect. The dosages of a pharmaceutically active ingredient which are useful in treatment when administered alone or in combination with one or more additional therapeutic agents are therapeutically effective amounts. Thus, as used herein, a therapeutically effective amount refers to an amount of therapeutic agent which produces the desired therapeutic effect as judged by clinical trial results and/or model animal studies. The therapeutically effective amount will vary depending on the compound, the disease, disorder or condition and its severity and the age, weight, etc., of the mammal to be treated. The dosage can be conveniently administered, e.g., in divided doses up to four times a day or in sustained-release form.

As used herein, the term "treat," "treatment," or "treating," refers to administering a therapeutic agent or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition. As used herein, a "therapeutic effect" relieves, to some extent, one or more of the symptoms of a disease or disorder. For example, a therapeutic effect may be observed by a reduction of the subjective discomfort that is communicated by a subject (e.g., reduced discomfort noted in self-administered patient questionnaire).

As used herein, the term "prophylaxis," "prevent," "preventing," "prevention," and grammatical variations thereof as used herein refers the preventive treatment of a subclinical disease-state in a subject, e.g., a mammal (including a human), for reducing the probability of the occurrence of a clinical disease-state. The method can partially or completely delay or preclude the onset or recurrence of a disorder or condition and/or one or more of its attendant symptoms or barring a subject from acquiring or reacquiring a disorder or condition or reducing a subject's risk of acquiring or requiring a disorder or condition or one or more of its attendant symptoms. The subject is selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, each of the terms "partial response" and "partial remission" can refer to the amelioration of a cancerous state, as measured by, for example, tumor size and/or cancer marker levels, in response to a treatment. In some embodiments, a "partial response" means that a tumor or tumor-indicating blood marker has decreased in size or level by about 50% in response to a treatment. The treatment can be any treatment directed against cancer, including but not limited to, chemotherapy, radiation therapy, hormone therapy, surgery, cell or bone Marrow transplantation, and immunotherapy. The size of a tumor can be detected by clinical or by radiological means. Tumor-indicating markers can be detected by means well known to those of skill, e.g., ELISA or other antibody-based tests.

As used herein, each of the terms "complete response" or "complete remission" means that a cancerous state, as measured by, for example, tumor size and/or cancer marker levels, has disappeared following a treatment, including but are not limited to, chemotherapy, radiation therapy, hormone therapy, surgery, cell or bone marrow transplantation, and immunotherapy. The presence and/or size of a tumor can be detected by clinical or by radiological means. Tumor-indicating markers can be detected by means well known to those of skill, e.g., ELISA or other antibody-based tests. A "complete response" does not necessarily indicate that the cancer has been cured, however, as a complete response can be followed by a relapse.

Cancer

Methods, compositions and kits disclosed herein can be used for treating cancer, including metastatic cancer. In some embodiments, a method for treating cancer comprises administrating an anti-angiogenics (e.g., bevacizumab) and a PLK1 inhibitor (e.g., onvansertib), or a pharmaceutically acceptable salt, solvate, stereoisomer, or prodrug thereof, to a subject in need thereof (e.g., a subject with metastatic cancer). In some embodiments, the subject has not received any prior treatment for inhibiting angiogenesis (for example, the subject has not received any prior treatment using bevacizumab alone, or the subject has not received any prior treatment using bevacizumab with one or more anticancer agents or one or more anticancer therapy (e.g., chemotherapy)). In some embodiments, the subject has not received any prior cancer treatment. The subject can, for example, be a subject who has no prior cancer diagnosis. In some embodiments, the subject has not received any prior treatment using bevacizumab and/or chemotherapies.

The methods, compositions and kits disclosed herein can be used to various types of cancer. The cancer can be a solid tumor, a liquid tumor, or a combination thereof. In some embodiments, the cancer is a solid tumor, including but not limited to, melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, Merkel cell carcinoma, brain and central nervous system cancers, and any combination thereof. In some embodiments, the cancer is a liquid tumor. In some embodiments, the cancer is a hematological cancer. Non-limiting examples of hematological cancer include Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), and Multiple myeloma ("MM"). Additionally, the disease or condition provided herein includes refractory or recurrent malignancies whose growth may be inhibited using the methods and compositions disclosed herein.

In some embodiments, the cancer is a metastatic cancer. As used herein, "metastatic cancer" can refer to when a cancer spreads (metastasizes) from its original site to another area of the body. Virtually all cancers have the potential to spread this way. Whether metastases develop depends on the complex interaction of many tumor cell factors, including the type of cancer, the degree of maturity (differentiation) of the tumor cells, the location and how long the cancer has been present, as well as other incompletely understood factors. As used herein, the term "metastasis" can refer to formation of progressively growing secondary tumor foci at sites discontinuous from the primary lesion. The metastatic process is a multi-step mechanism in which a metastatic cancer cell escapes from the primary tumor, enters the circulation, invades a distant tissue site and grows into a macroscopic tumor at the target site. The metastatic cancer can be metastatic colorectal cancer, metastatic bladder cancer, metastatic breast cancer, metastatic kidney cancer, metastatic lung cancer, metastatic ovarian cancer, metastatic pancreatic cancer, metastatic prostate cancer, metastatic stomach cancer, metastatic thyroid cancer, metastatic uterine cancer, metastatic renal cancer, metastatic cervical cancer, metastatic recurrent glioblastoma, or a combination thereof.

PLK1 Inhibitors

Polo-like kinases (PLK) are a family of five highly conserved serine/threonine protein kinases. PLK1 is a master regulator of mitosis and is involved in several steps of the cell cycle, including mitosis entry, centrosome maturation, bipolar spindle formation, chromosome separation, and cytokinesis. PLK1 has been shown to be overexpressed in solid tumors and hematologic malignancies, including AML. PLK1 inhibition induces G2-M-phase arrest with subsequent apoptosis in cancer cells, and has emerged as a promising targeted therapy. Several PLK inhibitors have been studied in clinical trials. In a randomized phase II study of patients with AML who were treatment naïve yet unsuitable for induction therapy, the pan-PLK inhibitor, volasertib (BI6727), administered intravenously in combination with LDAC showed a significant increase in OS when compared with LDAC alone. A subsequent randomized phase III study identified no benefit of the combination and described an increased risk of severe infections. PLK1 facilitates HR during Double Strand DNA Break (DSB) Repair. PLK1 phosphorylates Rad51 and BRCA1, facilitating their recruitment to DSB sites and thereby HR-mediated DNA repair. The PLK1 inhibitor can be selective and/or specific for PLK1.

The PLK1 inhibitor can be a dihydropteridinone, a pyridopyrimidine, a aminopyrimidine, a substituted thiazolidinone, a pteridine derivative, a dihydroimidazo[1,5-f]pteridine, a metasubstituted thiazolidinone, a benzyl styryl sulfone analogue, a stilbene derivative, or any combination thereof. The PLK1 inhibitor can be onvansertib, BI2536, Volasertib (BI 6727), GSK461364, AZD1775, CYC140, HMN-176, HMN-214, rigosertib (ON-01910), MLN0905, TKM-080301, TAK-960, or Ro3280.

Onvansertib (also known as PCM-075, NMS-1286937, NMS-937, "compound of formula (I)" in U.S. Pat. No. 8,927,530, IUPAC name 1-(2-hydroxyethyl)-8-{[5-(4-methylpiperazin-1-yl)-2-(trifluoromethoxy)phenyl]amino}-4,5-dihydro-1H-pyrazolo[4,3-h]quinazoline-3-carboxamide) is a selective ATP-competitive PLK1 inhibitor. Biochemical assays demonstrated high specificity of onvansertib for PLK1 among a panel of 296 kinases, including other PLK members. Onvansertib has potent in vitro and in vivo antitumor activity in models of both solid and hematologic malignancies. Onvansertib is the first PLK1 specific ATP competitive inhibitor administered by oral route to enter clinical trials with proven antitumor activity in different preclinical models. Onvansertib inhibited cell proliferation at nanomolar concentrations in AML cell lines and tumor growth in xenograft models of AML. Onvansertib also significantly increased cytarabine antitumor activity in disseminated models of AML.

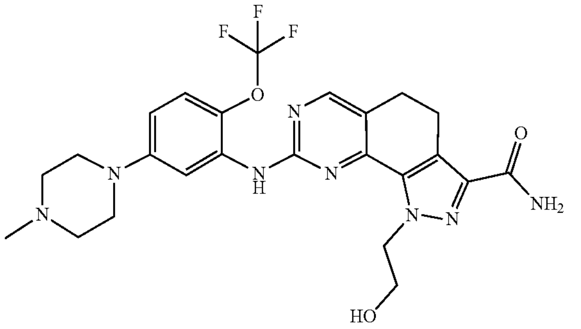

Onvansertib

Onvansertib shows high potency in proliferation assays having low nanomolar activity on a large number of cell lines, both from solid as well as hematologic tumors. Onvansertib potently causes a mitotic cell-cycle arrest followed by apoptosis in cancer cell lines and inhibits xenograft tumor growth with a clear PLK1-related mechanism of action at well tolerated doses in mice after oral administration. In addition, onvansertib shows activity in combination therapy with approved cytotoxic drugs, such as irinotecan, in which there is enhanced tumor regression in HT29 human colon adenocarcinoma xenografts compared to each agent alone, and shows prolonged survival of animals in a disseminated model of AML in combination therapy with cytarabine. Onvansertib has favorable pharmacologic parameters and good oral bioavailability in rodent and nonrodent species, as well as proven antitumor activity in different nonclinical models using a variety of dosing regimens, which may potentially provide a high degree of flexibility in dosing schedules, warranting investigation in clinical settings. Onvansertib has several advantages over volasertib (BI6727, another PLK1 inhibitor), including a higher degree of potency and specificity for the PLK1 isozyme, and oral bioavailability.

A phase I, first-in-human, dose-escalation study of onvansertib in patients with advanced/metastatic solid tumors identified neutropenia and thrombocytopenia as the primary dose-limiting toxicities. These hematologic toxicities were anticipated on the basis of the mechanism of action of the drug and were reversible, with recovery occurring within 3 weeks. The half-life of onvansertib was established between 20 and 30 hours. The oral bioavailability of onvansertib plus its short half-life provide the opportunity for convenient, controlled, and flexible dosing schedules with the potential to minimize toxicities and improve the therapeutic window. Pharmacodynamics and biomarker studies, including baseline genomic profiling, serial monitoring of mutant allele fractions in plasma, and the extent of PLK1 inhibition in circulating blasts, have been performed to identify biomarkers associated with clinical response and are described in WO2021/146322, the content of which is incorporated herein by reference in its entirety.

The cancer treatment of the present disclosure can comprise administration of a PLK1 inhibitor (e.g., onvansertib) to a subject with cancer for a desired duration in a cycle, two cycles, or more cycles. The desired duration in each cycle can independently be one, two, three, four, five, six, seven, eight, nine, ten, or more days. The cycle can be, for example, at least 20 days, 21 days, 22 days, 23 days, 24 days, 25 days, or more, in length. For example, a single cycle of the treatment can comprise administration of the PLK1 inhibitor (e.g., onvansertib) for four days, five days, six days, seven days, eight days, nine days, ten days, eleven days, twelve days, thirteen days, fourteen days, fifteen days, sixteen days, seventeen days, eighteen days, nineteen days, twenty days, or more in a cycle (e.g., a cycle of at least 21 days (e.g., 21 to 28 days)). In some embodiments, the treatment can comprise administration of the PLK1 inhibitor (e.g., onvansertib) for, or for at least, four days, five days, six days, seven days, eight days, nine days, ten days, eleven days, twelve days, thirteen days, fourteen days, fifteen days, sixteen days, seventeen days, eighteen days, nineteen days, twenty days, or a range between any two of these values, in a cycle (e.g., a cycle of at least 21 days (e.g., 21 to 28 days)). The administration of the PLK1 inhibitor (e.g., onvansertib) in a single cycle of the treatment can be continuous or with one or more intervals (e.g., one day or two days of break). In some embodiments, the treatment comprises administration of the PLK1 inhibitor (e.g., onvansertib) for five days in a cycle of 21 to 28 days. In some embodiments, the duration of administration of the PLK1 inhibitor in one cycle can be different from the duration of the administration of the PLK1 inhibitor in one or more other cycles. For example, the PLK1 inhibitor can be administered to the subject for 10 days (e.g., day 1 to day 5 in the first 14 days and day 1 to day 5 in the last 14 days in a 28-day cycle) for the first cycle, and for 14 days in the second cycle (e.g., day 1 to day 7 in the first 14 days and day 1 to day 7 in the last 14 days in a 28-day cycle). The length of each of the cycles can vary. For example, cycle 1 can be 28 days, and cycle 2 can be 21 days.

The cancer treatment disclosed herein can comprise administration of the PLK1 inhibitor (e.g., onvansertib) at, or at about, 12 $mg/m^2$-90 $mg/m^2$, for example, as a daily dose. For example, the treatment can comprise daily administration of the PLK1 inhibitor (e.g., onvansertib) at, or at about, 8 $mg/m^2$, 10 $mg/m^2$, 12 $mg/m^2$, 14 $mg/m^2$, 15 $mg/m^2$, 16 $mg/m^2$, 18 $mg/m^2$, 20 $mg/m^2$, 23 $mg/m^2$, 27 $mg/m^2$, 30 $mg/m^2$, 35 $mg/m^2$, 40 $mg/m^2$, 45 $mg/m^2$, 50 $mg/m^2$, 55 $mg/m^2$, 60 $mg/m^2$, 65 $mg/m^2$, 70 $mg/m^2$, 80 $mg/m^2$, 85 $mg/m^2$, 90 $mg/m^2$, a range between any two of these values, or any value between 8 $mg/m^2$-90 $mg/m^2$. In some embodiments, the daily dose of the PLK1 inhibitor (e.g., onvansertib) can be adjusted (e.g., increased or decreased with the range) during the treatment, or during a single cycle (e.g., the first cycle, the second cycle, the third cycle, and a subsequent cycle) of the treatment, for the subject. In some embodiments, the daily dose of the PLK1 inhibitor (e.g., onvansertib) is 12 $mg/m^2$, 15 $mg/m^2$, 18 $mg/m^2$, or 24 $mg/m^2$. In some embodiments, the daily dose of the PLK1 inhibitor (e.g., onvansertib) is 15 $mg/m^2$. The daily dose of the PLK1 inhibitor (e.g., onvansertib) for each cycle of treatment can vary. For example, the daily dose of the PLK1 inhibitor (e.g., onvansertib) for the first cycle can be 12 $mg/m^2$, and the daily dose of the PLK1 inhibitor (e.g., onvansertib) for the second cycle can be increased to, for example, 15 $mg/m^2$. In some embodiments, the daily dose of the PLK1 inhibitor (e.g., onvansertib) for the second cycle can then be increased to, for example, 18 $mg/m^2$. Without being bound by any particular theory, it is believed that the $mg/m^2$ doses disclosed herein are Body Surface Area (BSA) based doses corresponding to flat doses in the range of 20 to 45 mg.

A maximum concentration ($C_{max}$) of the PLK1 inhibitor (e.g., onvansertib) in a blood of the subject (during the treatment or after the treatment) when the PLK1 inhibitor is administered alone or in combination with one or more additional cancer therapeutics (e.g., FOLFIRI and bevacizumab) can be from about 100 nmol/L to about 1500 nmol/L. For example, the $C_{max}$ of the PLK1 inhibitor (e.g., onvansertib) in a blood of the subject when the PLK1 inhibitor is administered alone or in combination with one or more additional cancer therapeutics (e.g., FOLFIRI and bevacizumab) can be, or be about, 100 nmol/L, 200 nmol/L, 300 nmol/L, 400 nmol/L, 500 nmol/L, 600 nmol/L, 700 nmol/L, 800 nmol/L, 900 nmol/L, 1000 nmol/L, 1100 nmol/L, 1200 nmol/L, 1300 nmol/L, 1400 nmol/L, 1500 nmol/L, a range between any two of these values, or any value between 200 nmol/L to 1500 nmol/L.

An area under curve (AUC) of a plot of a concentration of the PLK1 inhibitor (e.g., onvansertib) in a blood of the subject over time (e.g., $AUC_{0-24}$ for the first 24 hours after administration) when the PLK1 inhibitor is administered alone or in combination with one or more additional cancer therapeutics (e.g., FOLFIRI and bevacizumab) can be from about 1000 nmol/L.hour to about 400000 nmol/L.hour. For example, the AUC of a plot of a concentration of the PLK1 inhibitor (e.g., onvansertib) in a blood of the subject over time (e.g., $AUC_{0-24}$ for the first 24 hours after administration) when the PLK1 inhibitor is administered alone or in combination with one or more additional cancer therapeutics (e.g., FOLFIRI and bevacizumab) can be, or be about, 1000 nmol/L.hour, 5000 nmol/L.hour, 10000 nmol/L.hour, 15000 nmol/L.hour, 20000 nmol/L.hour, 25000 nmol/L.hour, 30000 nmol/L.hour, 35000 nmol/L.hour, 40000 nmol/L.hour, a range between any two of these values, or any value between 1000 nmol/L.hour and 400000 nmol/L.hour.

A time ($T_{max}$) to reach a maximum concentration of the PLK1 inhibitor (e.g., onvansertib) in a blood of the subject when the PLK1 inhibitor is administered alone or in combination with one or more additional cancer therapeutics (e.g., FOLFIRI and bevacizumab) can be from about 1 hour to about 5 hours. For example, the time ($T_{max}$) to reach a maximum concentration of the PLK1 inhibitor (e.g., onvansertib) in a blood of the subject when the PLK1 inhibitor is administered alone or in combination with the one or more additional cancer therapeutics (e.g., FOLFIRI and bevacizumab) can be, or be about, 1 hour, 1.5 hours, 2 hours, 2.5 hours, 3 hours, 3.5 hours, 4 hours, 4.5 hours, 5 hours, a range between any two of these values, or any value between 1 hour and 5 hours.

An elimination half-life ($T_{1/2}$) of the PLK1 inhibitor (e.g., onvansertib) in a blood of the subject when the PLK1 inhibitor is administered alone or in combination with one or more additional cancer therapeutics (e.g., FOLFIRI and bevacizumab) can be from about 10 hours to about 60 hours. For example, the elimination half-life ($T_{1/2}$) of the PLK1 inhibitor (e.g., onvansertib) in a blood of the subject when the PLK1 inhibitor is administered alone or in combination with one or more additional cancer therapeutics (e.g., FOLFIRI and bevacizumab) can be, or be about, 10 hours, 15 hours, 20 hours, 25 hours, 30 hours, 35 hours, 40 hours, 45 hours, 50 hours, 55 hours, 60 hours, a range between any two of these values, or any value between 10 hours and 60 hours.

Anti-Angiogenics

Angiogenesis is known as the inappropriate formation of new blood vessels, and is typically required for cancer metastasis. "Angiogenesis" often occurs in tumors when endothelial cells secrete a group of growth factors that are mitogenic for endothelium causing the elongation and proliferation of endothelial cells which results in a generation of new blood vessels. The inhibition of angiogenesis can cause tumor regression in animal models and has also been found to be effective in humans for treatment of metastatic cancer. The terms "anti-angiogenics" and "angiogenesis inhibitor" shall have their ordinary meaning, and can also be used interchangeably herein to refer to any agent that can inhibit angiogenesis. Several anti-angiogenics have been approved for use in humans for the treatment of cancer. In some embodiments of the methods disclosed herein, the subject has not received any prior treatment comprising administration of an angiogenesis inhibitor.

The angiogenesis inhibitor and/or the anti-angiogenics can be capable of inhibiting VEGF-A, VEGFR-1, VEGFR-2, VEGFR-3, EGFR, HER2, PDGFR family proteins, RAF, Kit (or c-Kit), FLT3, CSF-1R, RET, Abl, Itk, LcK, c-FMS, FGFR family proteins, c-Met, PIGF, TNF-α, IFNs, ILs, bFGF, mTOR, or any combination thereof. The anti-angiogenics can be Afatinib (Gilotrif®), Axitinib (Inlyta®), bevacizumab (Avastin®), Cabozantinib (Cometriq®), Cetuximab (Erbitux®), Erlotinib (Tarceva®), Everolimus (Afinitor®), Gefitinib (Iressa®), Imatinib (Gleevec®), Lapatinib (Tykerb®), Lenalidomide (Revlimid®), Lenvatinib mesylate (Lenvima®), Necitumumab (Portrazza™), Neratinib (Nerlynx®), Panitumumab (Vectibix®), Pazopanib (Votrient®), Pertuzumab (Perjeta®), Ramucirumab (Cyramza®), Regorafenib (Stivarga®), Sorafenib (Nexavar®), Sunitinib (Sutent®), Thalidomide (Synovir, Thalomid®), Trastuzumab (Ontruzant®), Vandetanib (Caprelsa®), or Ziv-aflibercept (Zaltrap®). The angiogenesis inhibitor can be Afatinib (Gilotrif®), Axitinib (Inlyta®), bevacizumab (Avastin®), Cabozantinib (Cometriq®), Cetuximab (Erbitux®), Erlotinib (Tarceva®), Everolimus (Afinitor®), Gefitinib (Iressa®), Imatinib (Gleevec®), Lapatinib (Tykerb®), Lenalidomide (Revlimid®), Lenvatinib mesylate (Lenvima®), Necitumumab (Portrazza™), Neratinib (Nerlynx®), Panitumumab (Vectibix®), Pazopanib (Votrient®), Pertuzumab (Perjeta®), Ramucirumab (Cyramza®), Regorafenib (Stivarga®), Sorafenib (Nexavar®), Sunitinib (Sutent®), Thalidomide (Synovir, Thalomid®), Trastuzumab (Ontruzant®), Vandetanib (Caprelsa®), or Ziv-aflibercept (Zaltrap®).

Bevacizumab (also referred to herein as "bev") can be used in combination with chemotherapy in both $1^{st}$ and $2^{nd}$ lines of therapy for treating cancer. Other anti-angiogenics, e.g., ramucirumab and aflibercept, can be used in $2^{nd}$ line setting. Prior to the presently disclosed method, overall survival (OS) and median progression free survival (mPFS) benefit in $2^{nd}$ line have been shown to be independent of whether bevacizumab was given in $1^{st}$ line (e.g., the subject received prior treatment comprising inhibiting angiogenesis). For example, in studies examining OS and PFS in patients with and without prior bevacizumab treatment, it was found that OS was 13.9 months without prior bevacizumab vs. 12.5 months with prior bevacizumab. For PFS, mPFS was 6.9 months without prior bevacizumab vs. 6.7 months with prior Bevacizumab. Anti-angiogenic therapies incrementally improve response rates in patients with prior bevacizumab vs without prior bevacizumab. The objective response rate of patients who had received prior bevacizumab is 5% to 13% as compared to ~25% with no prior bevacizumab.

As disclosed herein, a combination therapy of an anti-angiogenics and a PLK1 inhibitor (including onvansertib) can surprisingly result in significantly enhanced efficacy against metastatic cancer in a subject that has not received prior treatment comprising inhibiting angiogenesis (e.g., metastatic colorectal cancer, metastatic bladder cancer, metastatic breast cancer, metastatic kidney cancer, metastatic lung cancer, metastatic ovarian cancer, metastatic pancreatic cancer, metastatic prostate cancer, metastatic stomach cancer, metastatic thyroid cancer, metastatic uterine cancer, metastatic renal cancer, metastatic cervical cancer, metastatic recurrent glioblastoma, or a combination thereof), causing tumor regression and cancer survival. The resulting tumor regression and cancer survival rate/duration by the combination can be surprisingly synergistic (i.e., more than additive, superior to the cumulated anti-tumor efficacy caused by the anti-angiogenics and the PLK1 inhibitor separately). The PLK1 inhibitor can be onvansertib. Provided herein include methods, compositions and kits for treating metastatic cancer in a subject (e.g., a human patient suffering from metastatic cancer). Provided herein include methods, compositions and kits for treating cancer in a subject (for example, a human patient suffering from cancer) wherein the subject has not received any prior treatment comprising inhibiting angiogenesis. The method comprises administrating an anti-angiogenics and a PLK1 inhibitor to the patient in a manner sufficient to inhibit progression of the cancer. For example, the anti-angiogenics and the PLK1 inhibitor can be administrated to a subject with cancer simultaneously, separately, or sequentially.

In some embodiments, administering the PLK1 inhibitor and the anti-angiogenics synergistically reduces or inhibits progression of the metastatic cancer relative to the PLK1 inhibitor treatment alone, the anti-angiogenics treatment alone, and/or the additive effect of the PLK1 inhibitor treatment alone and the anti-angiogenics treatment alone.

The inhibition or reduction of cancer progression that can be achieved by the methods disclosed herein using the PLK1 inhibitor (e.g., onvansertib) and the anti-angiogenics (e.g., bevacizumab) is not merely additive, but is enhanced or synergistic (that is, the inhibition is greater than the combined inhibition of progression caused by the anti-angiogenics alone plus the PLK1 inhibitor alone). The enhanced or synergistic efficacy or inhibition of any combination of an anti-angiogenics and a PLK1 inhibitor of the present disclosure can be different in different embodiments. In some embodiments, the enhanced or synergistic efficacy or inhibition of any combination of an anti-angiogenics and a PLK1 inhibitor of the present disclosure is, is about, is at least, is at least about, is at most, or is at most about, 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 210%, 220%, 230%, 240%, 250%, 260%, 270%, 280%, 290%, 300%, or a number or a range between any two of these values, higher than the combined inhibition of progression caused by the anti-angiogenics alone plus the PLK1 inhibitor alone.

The molar ratio of the PLK1 inhibitor (e.g., onvansertib) to the anti-angiogenics (e.g., bevacizumab) can be, for example, about 1:200, 1:100, 1:90, 1:80, 1:70, 1:60, 1:50, 1:40, 1:30, 1:20, 1:10, 1:1, 10:1, 20:1, 30:1, 40:1, 50:1, 100:1, 1000:1, 2000:1, or 5000:1, or a number or a range between any two of these values. In some embodiments, the enhanced or synergistic efficacy or inhibition of cancer progression caused by a combination of the anti-angiogenics and the PLK1 inhibitor (e.g., onvansertib) is, is about, is at least, is at least about, is at most, or is at most about 20%, 30%, 40%, 50%, 60%, 70%, 80%, 90%, 100%, 110%, 120%, 130%, 140%, 150%, 160%, 170%, 180%, 190%, 200%, 250%, 300%, or a number or a range between any two of these values, higher than the combined inhibition of progression caused by the anti-angiogenics alone plus the PLK1 inhibitor (e.g., onvansertib) alone. For example, a combination of the anti-angiogenics and the PLK1 inhibitor can cause a 50%, 60%, 70%, 80%, 90%, or more, inhibition of cancer progression (cancer cell viability of 50%, 40%, 30%, 20%, 10%, or less), whereas under the same conditions the combined inhibition of the anti-angiogenics alone plus the PLK1 inhibitor alone can be 10%, 20%, 25%, 30%, or less) inhibition of cancer progression (cancer cell viability of 90%, 80%, 75%, 70%, or more). Thus, the enhanced or synergistic efficacy or inhibition of cancer progression caused by the combination of the anti-angiogenics and the PLK1 inhibitor for example, 50%, 60%, 70%, 80%, 90%, 100%, or more higher than the combined inhibition of progression caused by the anti-angiogenics alone plus the PLK1 inhibitor alone. In some embodiments, the anti-angiogenics is bevacizumab and the PLK1 inhibitor is onvansertib.

The anti-angiogenics and the PLK1 inhibitor can be administered to the patient in any manner deemed effective to treat the cancer. The anti-angiogenics can be administered together with, or separately from, the PLK1 inhibitor. When administered separately, the anti-angiogenics can be administered before or after the PLK1 inhibitor, or in different administration cycles. The administration of the PLK1 inhibitor can be oral administration. The administration of the anti-angiogenics can be intravenous administration or oral administration.

The PLK1 inhibitor and the anti-angiogenics can be administered simultaneously or sequentially. In some embodiments, it can be advantageous to administer the PLK1 inhibitor (e.g., onvansertib) to the subject before the anti-angiogenics (e.g., bevacizumab), e.g., on one or more days, or each day, of the days on which the PLK1 inhibitor and the anti-angiogenics are administered to the subject. The time interval between the administration of the PLK1 inhibitor and the administration of the anti-angiogenics can be, for example, 30 minutes, 1 hour, 2 hours, 3 hours, 4 hours, 5 hours, 6 hours, 7 hours, 8 hours, 9 hours, 10 hours, 11 hours, 12 hours, a range between any two of these values, or any value between 30 minutes and 12 hours. In some embodiments, the PLK1 inhibitor (e.g., onvansertib) and the anti-angiogenics (e.g., bevacizumab) are both administered to the subject on, or on at least about, 50%, 60%, 70%, 75%, 80%, 85%, 90%, 95%, or 100% of the days in a cycle (e.g., in each cycle during the combination treatment), and optionally the PLK1 inhibitor is administered to the subject prior to the anti-angiogenics on each of the days both are administered, for example the PLK1 inhibitor is administered 30 minutes, 1 hour, 2 hours, 3 hours, 4 hours, 5 hours, 6 hours, 7 hours, 8 hours, 9 hours, 10 hours, 11 hours, 12 hours, a range between any two of these values, or any value between 30 minutes and 12 hours, prior to the administration of the anti-angiogenics.

The anti-angiogenics and the PLK1 inhibitor can each be administered in any schedule, e.g., once or multiple times per day or week; once, twice, three times, four times, five times, six times or seven times (daily) per week; for one or multiple weeks; etc. In some embodiments, the anti-angiogenics and the PLK1 inhibitor are each administered to the patient in a cycle of at least twice within a week. In other embodiments, the anti-angiogenics and the PLK1 inhibitor are each administered to the patient in a cycle of at least five times within a week. In some embodiments, the PLK1 inhibitor is administered daily, and the anti-angiogenics are administered daily, weekly, bi-weekly, every four weeks, every five weeks, or monthly. In further embodiments, the patient undergoes at least two cycles of administration. The patient can undergo one cycle or more than one cycle of administrations, for example, two cycles, three cycles, three cycles, four cycles, five cycles, or more. Two adjacent cycles of administration can be continuous, i.e., no break between the last day of the first cycle and the first day of the second cycle. In some embodiments, two adjacent cycles of administration have a break between them, i.e., an interval between the last day of the first cycle and the first day of the second cycle. The break (i.e., the interval) can be or be at least, one day, two days, three days, five days, seven days, ten days, two weeks, three weeks, four weeks, one month, two months, three months, four months, five months, six months, or a number or a range between any two of these values. In some embodiments, the patient undergoes three or four cycles of administration in which each cycle comprises at least five times within a week (e.g., 5 days per week). Each of the cycle in a multi-cycle administration can have the same dosing schedule, or different. For example, one of the cycle in the multi-cycle administration can be five continuous days of daily administration of the PLK1 inhibitor and anti-angiogenics and two days of break in one week for four weeks, and one or more other cycles in the same multi-cycle administration be 28 continuous days of daily administration of the PLK1 inhibitor and the anti-angiogenics in a four-week period. The PLK1 inhibitor can be administered on at least four days in the cycle. In some embodiments, PLK1 inhibitor is not administered on at least one day in the cycle.

The anti-angiogenics can be administered to the patient at any appropriate dosage, e.g., a dosage of about, at least or at most 0.1 mg/kg, 1 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 200 mg/kg, 300 mg/kg, 400 mg/kg, 500 mg/kg, 600 mg/kg, 700 mg/kg, 800 mg/kg, 900 mg/kg, 1000 mg/kg, 1500 mg/kg, 2000 mg/kg, or a number between any two of these values. The dosage unit based on the body weight (mg/kg) can be converted to another unit (e.g., $mg/m^2$) using a conversion chart such as the body surface area (BSA) conversion chart as will be understood by a person of skill in the art. The anti-angiogenics (e.g., bevacizumab) can be administered at about 1 mg/kg-20 mg/kg. In some embodiments, the anti-angiogenics is bevacizumab, which is administered at a dosage of about, at least or at most 1 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 200 mg/kg, 300 mg/kg, 400 mg/kg, 500 mg/kg, 600 mg/kg, 700 mg/kg, 800 mg/kg, 900 mg/kg, 1000 mg/kg, or a number between any two of these values. Bevacizumab can be administered at about 5 mg/kg, about 7.5 mg/kg, about 10 mg/kg, or about 15 mg/kg.

The anti-angiogenics can be administrated to the patient once daily, twice daily, or three times daily. The anti-angiogenics can be administered daily, weekly, bi-weekly, every three weeks, every four weeks, or every month. In some embodiments, the anti-angiogenics is administered in a cycle of 7-56 days of daily, weekly, bi-weekly, tri-weekly, every four weeks, or monthly. In some embodiments, the anti-angiogenics is administered in a cycle of 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 32 days, 35 days, 42 days, 49 days, or 56 days. In some embodiments, the anti-angiogenics is administered in 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 32 days, 35 days, 42 days, 49 days, or 56 days, in a cycle. In some embodiments, the anti-angiogenics is administered in day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, day 30, day 31, day 32, day 33, day 34, day 35, day 36, day 37, day 38, day 39, day 40, day 41, day 42, day 43, day 44, day 45, day 46, day 47, day 48, day 49, day 50, day 51, day 52, day 52, day 53, day 54, day 55, and/or day 56. In some embodiments, the anti-angiogenics is not administered in day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, day 31, day 32, day 33, day 34, day 35, day 36, day 37, day 38, day 39, day 40, day 41, day 42, day 43, day 44, day 45, day 46, day 47, day 48, day 49, day 50, day 51, day 52, day 52, day 53, day 54, day 55, and/or day 56.

In some embodiments, the subject has not received any prior treatment comprising administration of an angiogenesis inhibitor. The angiogenesis inhibitor can be the same as the anti-angiogenics. Any agent that can inhibit angiogenesis (e.g., an anti-angiogenic), now known or later discovered, can be used in these methods, including anti-angiogenics that inhibit the activity of one or more growth factors or any other protein that promotes angiogenesis. For example, the angiogenesis inhibitor and/or the anti-angiogenics can be capable of inhibiting vascular endothelial growth factor family proteins or the signaling pathways of said proteins such as VEGF-A, VEGFR-1, VEGFR-2, VEGFR-3, and PIGF. Other proteins and pathways that can be targeted by anti-angiogenics include, but are not limited to: epidermal growth factor receptor (EGFR), human epidermal growth factor receptor 2 (HER2), platelet-derived growth factor receptor (PDGFR) family proteins, RAF kinases; tyrosine kinases including Kit (or c-Kit), RET, Abl, Itk, LcK, c-Met, and FLT3; colony stimulating factor 1 receptor (CSF-1R) and c-FMS, fibroblast growth factor receptor (FGFR) family proteins, tumor necrosis factor alpha (TNF-$\alpha$), interferons (IFNs), interleukins (ILs), basic fibroblast growth factor (bFGF), mammalian target of rapamycin (mTOR), or any combination thereof. The anti-angiogenic can be a small molecule, an antibody or fragment thereof, an aptamer, an RNA (e.g., a miRNA), or any other agent capable of inhibiting angiogenesis. In some embodiments, the anti-angiogenic or angiogenesis inhibitor is bevacizumab (e.g., Avastin®).

Similarly, any PLK1 inhibitor, now known or later discovered, can be used in these methods, including PLK1 inhibitors that are selective for PLK1, and PLK1 inhibitors that also inhibit the activity of other proteins. In some embodiments, the PLK1 inhibitor is a dihydropteridinone, a pyridopyrimidine, a aminopyrimidine, a substituted thiazolidinone, a pteridine derivative, a dihydroimidazo[1,5-f] pteridine, a metasubstituted thiazolidinone, a benzyl styryl sulfone analogue, a stilbene derivative, or a combination thereof. In some of these embodiments, the PLK1 inhibitor is onvansertib, BI2536, Volasertib (BI 6727), GSK461364, AZD1775, CYC140, HMN-176, HMN-214, rigosertib (ON-01910), MLN0905, TKM-080301, TAK-960 or Ro3280.

The PLK1 inhibitor can be onvansertib. In these embodiments, onvansertib is administered to the patient at any appropriate dosage, e.g., a dosage of less than 12 mg/m$^2$, less than or equal to 24 mg/m$^2$, or greater than 24 mg/m$^2$. In some embodiments, onvansertib is administered to the patient at about 12 mg/m$^2$, at about 15 mg/m$^2$, or at about 18 mg/m$^2$. In some embodiments, the onvansertib is administered to the patient daily. In additional embodiments, onvansertib is administered in a cycle of 3-10 days of daily onvansertib administration with 2-16 days with no onvansertib administration. In some embodiments, onvansertib is administered to the patient in a cycle of at least five times within a week. The patient can undergo two, three, or four cycles of administration. In some embodiments, the patient undergoes four cycles of administration in a cycle of at least five days of daily onvansertib administration with 1-2 days with no onvansertib administration.

In some embodiments, a PLK1 inhibitor alone or in combination with an anti-angiogenics is administrated to a patient who has taken a drug holiday after undergoing one or more cycles of administration. A drug holiday as used herein refers to a period of time when a patient stops taking a PLK1 inhibitor and/or an anti-angiogenics. A drug holiday can be a few days to several months. In some embodiments, the drug holiday can be 1 week, 2 weeks, 3 weeks, 4 weeks, 5 weeks, 6 weeks, 7 weeks, 8 weeks, 9 weeks, 10 weeks, or any value or a range between any two of these values.

As can be appreciated by one of skill in the art, the amount of administration of the anti-angiogenics and the PLK1 inhibitor, and the timing of the administration, can depend on the type (species, gender, age, weight, etc.) and condition of the subject being treated and the severity of the disease or condition being treated. The anti-angiogenics and the PLK1 inhibitor can formulated into a single pharmaceutical composition, or two separate pharmaceutical compositions. The active ingredients may also be entrapped in microcapsules prepared, for example, by coacervation techniques or by interracial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions.

Methods, compositions, kits and systems disclosed herein can be applied to different types of subjects. For example, the subject can be a subject receiving a cancer treatment, a subject at cancer remission, a subject has received one or more cancer treatment, or a subject suspected of having cancer. The subject can have a stage I cancer, a stage II cancer, a stage III cancer, and/or a stage IV cancer. In some embodiments, the subject has stage IV cancer. In some embodiments, the subject has metastatic cancer. In some embodiments, the subject has not received any prior treatment comprising inhibiting angiogenesis.

The treatment of the present disclosure can comprise administration of a PLK1 inhibitor (onvansertib) for a desired duration in a cycle. The administration of the PLK1 inhibitor (and/or the anti-angiogenics) can be daily or with break(s) between days of administrations. The break can be, for example, 1 day, 2 days, 3 days, 4 days, 5 days, 6 days, 7 days, 8 days, 9 days, 10 days, 11 days, 12 days, 13 days, 14 days, or more. The administration can be once, twice, three times, four times, or more on a day when the PLK1 inhibitor (and/or the anti-angiogenics) is administered to the patient. The administration can be, for example, once every two days, every three days, every four days, every five days, every six days, or every seven days. The length of the desired duration can vary, for example, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, or more days. Each cycle of treatment can have various lengths, for example, at least 14 days, 15 days, 16 days, 17 days, 18 days, 19 days, 20 days, 21 days, 22 days, 23 days, 24 days, 25 days, 26 days, 27 days, 28 days, or more. For example, a single cycle of the treatment can comprise administration of the PLK1 inhibitor (e.g., onvansertib) and/or the anti-angiogenics agents for four days, five days, six days, seven days, eight days, nine days, ten days, eleven days, twelve days, thirteen days, fourteen days, fifteen days, sixteen days, seventeen days, eighteen days, nineteen days, twenty days, twenty-one days, twenty-two days, twenty-three days, twenty-four days, twenty-five days, twenty-six days, twenty-seven days, twenty-eight days, or more in a cycle (e.g., in a cycle of at least 21 days (e.g., 21 to 28 days)). In some embodiments, the treatment can comprise administration of the PLK1 inhibitor (e.g., onvansertib) and/or the anti-angiogenics for, or for at least, four days, five days, six days, seven days, eight days, nine days, ten days, eleven days, twelve days, thirteen days, fourteen days, fifteen days, sixteen days, seventeen days, eighteen days, nineteen days, twenty days, or a range between any two of these values, in a cycle (e.g., a cycle of at least 21 days (e.g., 21 to 28 days)). The administration of the PLK1 inhibitor (e.g., onvansertib) and/or the anti-angiogenics in a single cycle of the treatment can be continuous or with one or more intervals (e.g., one day or two days of break). In some embodiments, the treatment comprises administration of the PLK1 inhibitor (e.g., onvansertib) for five days in a cycle of 21 to 28 days.

In some embodiments, the PLK1 inhibitor (e.g., onvansertib) is administered to the subject in need thereof on twenty days (e.g., Days 1-10 and 15-24) during a 28-day cycle. The twenty days can be, for example, a continuous daily administration for ten days (e.g., Days 1-10) and another continuous daily administration (e.g., Days 15-24) for ten days, or a continuous daily administration for four sets of five days (e.g., Days 1-5, 8-12, 15-19, and 22-26), In some embodiments, for example when the patient is identified to have low tolerance to the PLK1 inhibitor, the PLK1 inhibitor is administered to the subject in need thereof on ten days (e.g., Days 1-5 and 15-19) during a 28-day cycle. The ten days can be, for example, a continuous daily administration for ten days (e.g., Days 1-10) or two continuous daily admiration for five days each (e.g., Days 1-5 and Days 15-19). In some embodiments, the PLK1 inhibitor is administered to the subject in need thereof daily throughout the whole cycle (e.g., daily for 28 days in a cycle of 28 days). Depending on the needs of inhibition/reversion of cancer progression in the subject, the subject can receive one, two, three, four, five, six, or more cycles of treatment. For combination treatment, the administration cycles, dosing schedules, and/or dosage amounts of the anti-angiogenics and the PLK1 inhibitor can be the same or different. For combination treatment, the administration cycle, dosing schedule, and/or dosage amount of the anti-angiogenics can be adjusted according to the administration cycle, dosing schedule, and/or dosage amount of the PLK1 inhibitor. For example, the anti-angiogenics (e.g., bevacizumab) can be administered in four 7-day cycles (e.g., daily dose on Days 1-5 and no dose on Days 6-7, repeated for 4 weeks), which corresponds to a 28-day cycle for administration of the PLK1 inhibitor (e.g., onvansertib).

The treatment can comprise administration of the PLK1 inhibitor (e.g., onvansertib) at, or at about, 6 $mg/m^2$-90 $mg/m^2$, for example, as a daily dose. For example, the treatment can comprise daily administration of the PLK1 inhibitor (e.g., onvansertib) at, or at about, 6 $mg/m^2$, 8 $mg/m^2$, 10 $mg/m^2$, 12 $mg/m^2$, 14 $mg/m^2$, 16 $mg/m^2$, 18 $mg/m^2$, 20 $mg/m^2$, 23 $mg/m^2$, 27 $mg/m^2$, 30 $mg/m^2$, 35 $mg/m^2$, 40 $mg/m^2$, 45 $mg/m^2$, 50 $mg/m^2$, 55 $mg/m^2$, 60 $mg/m^2$, 65 $mg/m^2$, 70 $mg/m^2$, 80 $mg/m^2$, 85 $mg/m^2$, 90 $mg/m^2$, a number or a range between any two of these values, or any value between 8 $mg/m^2$-90 $mg/m^2$. In some embodiments, the daily dose of the PLK1 inhibitor (e.g., onvansertib) can be adjusted (e.g., increased or decreased with the range) during the treatment, or during a single cycle (e.g., the first cycle, the second cycle, the third cycle, and a subsequent cycle) of the treatment, for the subject. In some embodiments, the PLK1 inhibitor (e.g., onvansertib) is administered at 12 $mg/m^2$ on twenty days (e.g., Days 1-10 and 15-24) during a 28-day cycle. In some embodiments, the PLK1 inhibitor (e.g., onvansertib) is administered at 15 $mg/m^2$ on ten days (e.g., Days 1-5 and 15-19) during a 28-day cycle. In some embodiments, the PLK1 inhibitor (e.g., onvansertib) is administered at 8 $mg/m^2$ or 10 $mg/m^2$ everyday (e.g., Days 11-28) during a 28-day cycle. In some embodiments, the daily dose of the PLK1 inhibitor (e.g., onvansertib) can be adjusted (e.g., increased or decreased with the range) during the treatment, or during a single cycle (e.g., the first cycle, the second cycle, the third cycle, and a subsequent cycle) of the treatment, for the subject. In some embodiments, the PLK1 inhibitor is administered at or at about 12 $mg/m^2$. In some embodiments, the PLK1 inhibitor is administered at or at about 15 $mg/m^2$. In some embodiments, the PLK1 inhibitor is administered at or at about 18 $mg/m^2$.

A maximum concentration (Cmax) of the PLK1 inhibitor (e.g., onvansertib) in a blood of the subject (during the treatment or after the treatment) when the PLK1 inhibitor is administered alone or in combination with the anti-angiogenics can be from about 100 nmol/L to about 1500 nmol/L. For example, the Cmax of the PLK1 inhibitor in a blood of the subject when the PLK1 inhibitor is administered alone or in combination with the anti-angiogenics can be, or be about, 100 nmol/L, 200 nmol/L, 300 nmol/L, 400 nmol/L, 500 nmol/L, 600 nmol/L, 700 nmol/L, 800 nmol/L, 900 nmol/L, 1000 nmol/L, 1100 nmol/L, 1200 nmol/L, 1300 nmol/L, 1400 nmol/L, 1500 nmol/L, a range between any two of these values, or any value between 200 nmol/L to 1500 nmol/L.

An area under curve (AUC) of a plot of a concentration of the PLK1 inhibitor (e.g., onvansertib) in a blood of the subject over time (e.g., $AUC_{0-24}$ for the first 24 hours after administration) when the PLK1 inhibitor is administered alone or in combination with the anti-angiogenics can be from about 1000 nmol/L.hour to about 400000 nmol/L.hour. For example, the AUC of a plot of a concentration of the PLK1 inhibitor in a blood of the subject over time (e.g., $AUC_{0-24}$ for the first 24 hours after administration) when the PLK1 inhibitor is administered alone or in combination with the anti-angiogenics can be, or be about, 1000 nmol/L.hour, 5000 nmol/L.hour, 10000 nmol/L.hour, 15000 nmol/L.hour, 20000 nmol/L.hour, 25000 nmol/L.hour, 30000 nmol/L.hour, 35000 nmol/L.hour, 40000 nmol/L.hour, a range between any two of these values, or any value between 1000 nmol/L.hour and 400000 nmol/L.hour.

A time ($T_{max}$) to reach a maximum concentration of the PLK1 inhibitor (e.g., onvansertib) in a blood of the subject when the PLK1 inhibitor is administered alone or in combination with the anti-angiogenics can be from about 1 hour to about 5 hours. For example, the time ($T_{max}$) to reach a maximum concentration of the PLK1 inhibitor in a blood of the subject when the PLK1 inhibitor is administered alone or in combination with the anti-angiogenics can be, or be about, 1 hour, 1.5 hours, 2 hours, 2.5 hours, 3 hours, 3.5 hours, 4 hours, 4.5 hours, 5 hours, a range between any two of these values, or any value between 1 hour and 5 hours.

An elimination half-life ($T_{1/2}$) of the PLK1 inhibitor (e.g., onvansertib) in a blood of the subject when the PLK1 inhibitor is administered alone or in combination with the anti-angiogenics can be from about 10 hours to about 60 hours. For example, the elimination half-life ($T_{1/2}$) of the PLK1 inhibitor in a blood of the subject when the PLK1 inhibitor is administered alone or in combination with the anti-angiogenics can be, or be about, 10 hours, 15 hours, 20 hours, 25 hours, 30 hours, 35 hours, 40 hours, 45 hours, 50 hours, 55 hours, 60 hours, a range between any two of these values, or any value between 10 hours and 60 hours.

As described herein, the methods, compositions and kits described herein can reduce or inhibit progression of the cancer. In some embodiments, the reduction or inhibition comprises inhibition of growth of one or more tumors in the subject and/or reducing the number of cancer cells detected in the subject by at least about 25%, 30%, 40%, 50%, 60%, or 70%; relative to an untreated subject. In some embodiments, the reduction or inhibition comprises inhibition of growth of one or more tumors in the subject and/or reducing the number of cancer cells detected in the subject by at least about 25%, 30%, 40%, 50%, 60%, or 70%; relative to the subject prior to administration of the PLK1 inhibitor and the anti-angiogenics. The growth of at least one of the one or more tumors in the subject can be, for example, reduced by at least about 25%, 30%, 40%, 50%, 60%, or 70% following one or more cycles of treatment. In some embodiments, the size/volume of at least one of the one or more tumors in the subject is reduced by at least about 25%, 30%, 40%, 50%, 60%, or 70% following one or more cycles of treatment.

Additional Cancer Therapeutics or Therapy

Methods, compositions and kits disclosed herein can be used for treating cancer. In some embodiments, a method for treating cancer (e.g., mCRC) comprises administrating an anti-angiogenics and a PLK1 inhibitor (e.g., onvansertib) to a subject (e.g., a patient) in need thereof. The method can comprise administering a therapeutically effective amount of the anti-angiogenics and a therapeutically effective amount of the PLK1 inhibitor. The treatment can comprise administration of at least one additional cancer therapeutics or cancer therapy. In some embodiments, the subject has not received any prior treatment comprising inhibiting angiogenesis. In some embodiments, the subject has not received any prior treatment for inhibiting angiogenesis (for example, the subject has not received any prior treatment using bevacizumab alone, or the subject has not received any prior treatment using bevacizumab with one or more anticancer agents or one or more anticancer therapy (e.g., chemotherapy)). In some embodiments, the subject has not received any prior cancer treatment. The subject can, for example, be a subject who has no prior cancer diagnosis. In some embodiments, the subject has not received any prior treatment using bevacizumab and/or chemotherapies.

Non-limiting examples of the additional cancer therapeutics or cancer therapy can include surgery, chemotherapy, radiation therapy (including external-beam, stereotactic, and intraoperative radiation therapy and brachytherapy), bone marrow transplant, immunotherapy, targeted drug therapy, cryoablation, or radiofrequency ablation. Where the cancer is colorectal cancer, examples of treatments include surgery, radiofrequency ablation, cryoablation, radiation therapy, chemotherapy (including medications comprising capecitabine, 5-fluorouracil (5-FU), irinotecan, oxaliplatin, trifluridine/tipiracil), targeted therapy (including anti-angiogenesis therapy using, for example bevacizumab, regorafenib, ziv-aflibercept, or ramucirumab; immunotherapy using, for example pembrolizumab, nivolumab, or ipilimumab; and PLK1 inhibitors).

The additional cancer therapeutics or cancer therapy can be a chemotherapy, for example, FOLFIRI, FOLFOX, XELOX (CAPOX), FOLFOXIRI, or a combination thereof. Chemotherapy regimens using fluorouracil are standard treatment for advanced colorectal cancer. Fluorouracil is a pyrimidine analog and antimetabolite, which incorporates into the DNA molecule and stops synthesis, thereby, preventing replication of cancer cells. Examples of these regimens include FOLFOX and FOLFIRI. The additional cancer therapeutics or cancer therapy can comprise a therapeutically effective amount of FOLFIRI. FOLFIRI is a chemotherapeutical cocktail, containing leucovorin (folinic acid), fluorouracil and irinotecan hydrochloride. Leucovorin is a vitamin B derivative and increases the cytotoxicity of fluorouracil in this combination. Irinotecan is a topoisomerase inhibitor, which prevents DNA from uncoiling and duplicating. FOLFIRI is often used in combination with other therapeutical reagents (e.g., bevacizumab) to improve efficacy and response rate.

FOLFOX is a chemotherapy regimen for treatment of colorectal cancer, made up of folinic acid, fluorouracil and oxaliplatin (Eloxatin). FOLFOX can be broken down into other subtypes such as FOLFOX-4, FOLFOX-6, and FOLFOX-7 depending on how these three drugs are administered. FOLFOX is usually used to treat colorectal cancer. It can also be used to treat pancreatic cancer and certain other cancers. FOLFOX is typically used as an adjuvant treatment (in addition to the primary therapy) for advanced cancers. However, FOLFOX can also be used as a first-line therapy for colorectal adenocarcinoma, which is the most common type of colon cancer. In this combination, oxaliplatin shows synergy with fluorouracil, with little toxicity overlap.

For decades, fluorouracil had been the only drug with demonstrated activity against colorectal cancer, commonly used in combination with leucovorin. Oxaliplatin and capecitabine are two relatively novel drugs used in the treatment of colorectal cancer. These drugs have been found to act synergistically, both in vivo and in vitro. The chemotherapy combination of oxaliplatin and capecitabine is known as XELOX, which is highly active in metastatic colorectal cancer (mCRC). Capecitabine has demonstrated high efficacy as first-line treatment for MCRC. It is an oral fluoropyrimidine that was rationally designed to generate FU preferentially at the tumor site, via a three-step enzymatic process that exploits the significantly higher activity of thymidine phosphorylase (TP) in tumors, compared with healthy tissue. Capecitabine causes less adverse effects, such as diarrhea, stomatitis, nausea, alopecia, and neutropenia, leading to less neutropenic fever/sepsis and associated hospitalizations compared to the combination therapy of leucovorin and fluorouracil (e.g., FOLFIRI, and FOLFOX), although hand-foot syndrome (HFS) occurred more frequently with capecitabine administration. Oxaliplatin is a third-generation cisplatin analog, and an organoplatinum complex, and is usually classified as alkylating agent although it is not capable of actually adding alkyl groups to DNA. Oxaliplatin is an integral component of the various fluorouracil regimens (e.g., FOLFOX), which have become a standard treatment for metastatic and node-positive colorectal cancer.

Another combination therapy of oxaliplatin and fluorouracil is known as FOLFOXIRI, containing leucovorin, fluorouracil, oxaliplatin and irinotecan. FOLFOXIRI is also an approved chemotherapy regimen for the treatment of advanced colorectal cancer and is often given with bevacizumab.

The additional cancer therapeutics can comprise FOLFIRI, bevacizumab, abiraterone, FOLFOX, an anti-EGFR agent, a KRAS directed inhibitor, gemcitabine, abraxane, nanoliposomal irinotecan, 5-FU, or a combination thereof. The PLK1 inhibitor and the cancer therapeutics or cancer therapy can be administered simultaneously or sequentially. In some embodiments, the additional cancer therapeutics or therapies comprises FOLFIRI, abiraterone, FOLFOX, an anti-EGFR agent, a KRAS directed inhibitor, gemcitabine, abraxane, nanoliposomal irinotecan, 5-FU, or a combination thereof. In some embodiments, anti-EGFR agents is optionally cetuximab. In some embodiments, the KRAS directed inhibitor is optionally a G12C inhibitor, a G12D inhibitor or a combination thereof. In some embodiments, the additional cancer therapy is FOLFOX (leucovorin, fluorouracil, and oxaliplatin), FOLFIRI (leucovorin, fluorouracil, and irinotecan), or a combination thereof.

Methods for Predicting/Determining Treatment Efficacy and Status for Cancer

Disclosed herein include methods of treating cancer. In some embodiments, the method comprises: administering a PLK1 inhibitor and an anti-angiogenics to a subject with a metastatic cancer, thereby reducing or inhibiting progression of the metastatic cancer, wherein the subject has not received any prior treatment comprising inhibiting angiogenesis. The method described herein using the combination of the anti-angiogenics and the PLK1 inhibitor is expected to be effective with various metastatic cancers, for example metastatic colorectal cancer, metastatic bladder cancer, metastatic breast cancer, metastatic kidney cancer, metastatic lung cancer, metastatic ovarian cancer, metastatic pancreatic cancer, metastatic prostate cancer, metastatic stomach cancer, metastatic thyroid cancer, metastatic uterine cancer, metastatic renal cancer, metastatic cervical cancer, metastatic recurrent glioblastoma, or a combination thereof.

The method can comprise one or more of (1) determining cancer status of the subject, (2) determining responsiveness of the subject to a PLK1 inhibitor treatment, and (3) administering one or more cancer therapeutics or therapies for the cancer.

In some embodiments, administering the PLK1 inhibitor and the anti-angiogenics improves one or more therapeutic effects in the treated subjects relative to a control or a baseline. The one or more therapeutic effects can comprise size of a tumor derived from the metastatic cancer, objective response rate (ORR), duration of response, time to response, progression free survival (PFS), overall survival (OS), disease control rate (DCR), oncogenic allelic burden, or a combination thereof. In some embodiments, administering the PLK1 inhibitor and the anti-angiogenics improves the ORR in the subjects, improves PFS in the treated subjects, improves OS in the treated subjects, improves DCR in the treated subjects, reduces oncogenic allelic burden in the treated subjects, or a combination thereof, relative to subjects who have received prior treatment comprising inhibiting angiogenesis.

Disclosed herein include methods of improving objective response rate (ORR), progression free survival (PFS), or both in subjects with a metastatic cancer. In some embodiments, the method comprises administering a PLK1 inhibitor and an anti-angiogenics to the subjects, thereby improving the ORR and/or the PFS of the subjects, wherein the subject has not received any prior treatment comprising inhibiting angiogenesis.

In some embodiments, administering the PLK1 inhibitor and the anti-angiogenics synergistically improves the ORR and/or the PFS of the treated subjects relative to the PLK1 inhibitor treatment alone, the anti-angiogenics treatment alone, and/or the additive effect of the PLK1 inhibitor treatment alone and the anti-angiogenics treatment alone.

Tumor evaluations and assessment of tumor burden and therapeutic efficacy can be made based on RECIST criteria (Therasse et al 2000), New Guidelines to Evaluate the Response to Treatment in Solid Tumors, Journal of National Melanoma Institute, Vol. 92; 205-16 and is made within the presently disclosed methods, in some embodiments, according to the revised RECIST guidelines (version 1.1) (Eisenhauer et al 2009, New response evaluation criteria in solid tumors: revised RECIST guideline (version 1.1). Eur J Melanoma, 45 (2): 228-47.), which is hereby incorporated by reference in its entirety.

In some embodiments, the treatment results in a sustained response in the subject after cessation of the treatment. "Sustained response" can refer to the sustained effect on reducing tumor growth after cessation of a treatment. For example, the tumor size may remain the same or smaller as compared to the size at the beginning of the administration phase. In some embodiments, the sustained response has a duration at least the same as the treatment duration, at least 1.5×, 2.0×, 2.5×, or 3.0×length of the treatment duration.

The treatment methods disclosed herein may result in a partial or complete response. As used herein, "complete response" or "CR" can refer to disappearance of all target lesions; "partial response" or "PR" can refer to at least a 30% decrease in the sum of the longest diameters (SLD) of target lesions, taking as reference the baseline SLD; and "stable disease" or "SD" can refer to neither sufficient shrinkage of target lesions to qualify for PR, nor sufficient increase to qualify for PD, taking as reference the smallest SLD since the treatment started. As used herein, "objective response rate" (ORR) can refer to the sum of complete response (CR) rate and partial response (PR) rate.

The treatment methods disclosed herein can lead to an increase in progression free survival (PFS) and overall survival (OS) of the subjects administered the combination therapy. As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease. As used herein, "overall survival" refers to the percentage of subjects in a group who are likely to be alive after a particular duration of time. As used herein, "disease control rate" refers to complete response (CR) plus partial response (PR) plus stable disease (SD).

In some embodiments, administering the PLK1 inhibitor and the anti-angiogenics improves the ORR in the subjects by, by about, by at least, or by at least about 50% (e.g., 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values) relative to subjects who have received prior treatment comprising inhibiting angiogenesis. In some embodiments, administering the PLK1 inhibitor and the anti-angiogenics improves the PFS in the subjects by, by about, by at least, or by at least about 50% (e.g., 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values) relative to subjects who have received prior treatment comprising inhibiting angiogenesis.

In some embodiments, administering a PLK1 inhibitor and an anti-angiogenics to a subject who has not received any prior treatment comprising inhibiting angiogenesis can result in an ORR of, of at least, of about, or of at least about 69% (e.g., 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values). In some embodiments, administering a PLK1 inhibitor and an anti-angiogenics to a subject who has received any prior treatment comprising inhibiting angiogenesis can result in an ORR of about 23% or less (e.g., 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, or a number or a range between any two of these values). In some embodiments, administering a PLK1 inhibitor and an anti-angiogenics to a subject who has not received any prior treatment comprising inhibiting angiogenesis can result in an median PFS of, of at least, of about, or of at least about 13.5 months (e.g., 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, 55 years, 60 years, 65 years, or more than 65 years). In some embodiments, administering a PLK1 inhibitor and an anti-angiogenics to a subject who has received any prior treatment comprising inhibiting angiogenesis can result in a median PFS of about 7.8 months or less (e.g., 1 month, 2 months, 3 months, 4 months, 5 months, 6 months, 7 months, 8 months, or a number or a range between any two of these values).

The term "inhibition of tumor growth" or "reduced tumor growth" can refer to causing a reduction in or complete cessation of tumor growth and/or causing a regression in tumor size (e.g., diameter and/or volume). The term "tumor volume" or "tumor size" can refer to the total size of the tumor, which can include the tumor itself plus affected lymph nodes if applicable. The presence or absence of a tumor, and tumor size can be determined by a variety of methods known in the art, such as, e.g. by measuring the dimensions of the tumor using calipers, computed tomography (CT) or magnetic resonance imaging (MRI) scans, mammography, and X-ray. The volume can be calculated using equations based on, for example, the z-axis diameter, or on standard shapes such as the sphere, ellipsoid, or cube. Tumor size may be assessed at any time before, during or following at least one cycle of treatment with onvansertib and/or anti-angiogenics. Tumor size can be assessed at a first timepoint, and at one or more additional timepoints. In some embodiments, tumor size can be assessed in the subject and, e.g., an untreated subject at equivalent timepoints (e.g., at a first timepoint, and at one or more additional timepoints). Tumor growth can be determined by, e.g., measuring tumor size at a first timepoint and measuring tumor size at one or more additional timepoints. In some embodiments, increased inhibition of tumor growth in the subject (e.g., improved ORR) indicates the subject as responsive to the cancer treatment.

The inhibition of growth of at least one of one or more tumors in the subject can be, can be about, can be at least, or can be at least about 1.1 times greater, 1.2 times greater, 1.3 times greater, 1.4 times greater, 1.5 times greater, 1.6 times greater, 1.7 times greater, 1.8 times greater, 1.9 times greater, 2 times greater, or a number or a range between any two of these values, or more, than the inhibition of growth caused by onvansertib and the anti-angiogenics in a subject who has received previous treatment for inhibiting angiogenesis, following one or more cycles of treatment. The inhibition of growth of at least one of the one or more tumors in the subject can be increased by, by about, by at least, or by at least about 25%, 30%, 35%, 40%, 50%, 55%, 60%, 65%, 70%, 75%, 80%, 85%, 90%, 95%, 100% or a number or a range between any two of these values, relative to a subject who has received previous treatment for inhibiting angiogenesis, following one or more cycles of treatment. The growth of at least one of the one or more tumors in the subject can be inhibited by, by about, by at least, or by at least about 50%, 55%, 60%, 65%, 70%, 75%, 80%, 85%, 90%, 95%, 100% or a number or a range between any two of these values relative to an untreated subject or a subject who has received prior anti-angiogenic treatment, following one or more cycles of treatment with the combination. The growth of at least one of the one or more tumors in the subject can be inhibited by, by about, by at least, or by at least about 70%, 75%, 80%, 85%, 90%, 95%, 100% or a number or a range between any two of these values relative to an untreated subject, following one or more cycles of treatment. The subject can be tumor-free following one or more cycles of treatment.

The inhibition of growth of at least one of the one or more tumors in the subject can be, can be about, can be at least, or can be at least about 1.1 times greater, 1.2 times greater, 1.3 times greater, 1.4 times greater, 1.5 times greater, 1.6 times greater, 1.7 times greater, 1.8 times greater, 1.9 times greater, 2 times greater, or a number or a range between any two of these values, or more, than the inhibition of growth caused by onvansertib alone or the anti-angiogenics alone, following one or more cycles of treatment. The inhibition of growth of at least one of the one or more tumors in the subject can be increased by, by about, by at least, or by at least about 25%, 30%, 35%, 40%, 50%, 55%, 60%, 65%, 70%, 75%, 80%, 85%, 90%, 95%, 100% or a number or a range between any two of these values, relative to a subject treated with onvansertib alone or the anti-angiogenics alone, following one or more cycles of treatment. The growth of at least one of the one or more tumors in the subject can be inhibited by, by about, by at least, or by at least about 50%, 55%, 60%, 65%, 70%, 75%, 80%, 85%, 90%, 95%, 100% or a number or a range between any two of these values relative to an untreated subject, following one or more cycles of treatment. The growth of at least one of the one or more tumors in the subject can be inhibited by, by about, by at least, or by at least about 70%, 75%, 80%, 85%, 90%, 95%, 100% or a number or a range between any two of these values relative to an untreated subject, following one or more cycles of treatment. The subject can be tumor-free following one or more cycles of treatment.

In some embodiments, the first time point is prior or immediately prior to the combination treatment, and at least one of the one or more additional time points are at the end of or after at least one cycle of the combination treatment. In some embodiments, the cycle of the combination treatment is the first cycle of the combination treatment. In some embodiments, the first time point is prior or immediately prior to a first cycle of the combination treatment, and the one or more additional time points are at the end of or after a second cycle of the combination treatment.

In some embodiments, the first cycle of the combination treatment is immediately prior to the second cycle of the combination treatment. In some embodiments, the method comprises continuing the combination treatment to the subject if the subject is indicated as responsive to the combination treatment. In some embodiments, the method comprises discontinuing the combination treatment to the subject and/or starting a different combination treatment to the subject if the subject is not indicated as responsive to the combination treatment.

The first time point can be prior or immediately prior to the combination treatment, and the one or more additional time points are at the end of or after at least a cycle of the combination treatment, optionally the cycle of the combination treatment is the first cycle of the combination treatment. In some embodiments, the first time point is prior or immediately prior to a first cycle of the combination treatment, and the one or more additional time points are at the end of or after a second cycle of the combination treatment, optionally the first cycle of the combination treatment is immediately prior to the second cycle of the combination treatment.

Determining the responsiveness of the subject can comprise determining if the subject is a responder of the treatment, if the subject is or is going to be in complete recovery (CR), or if the subject is or is going to be in partial remission (PR). Determining the responsiveness of the subject can comprise determining objective response rate (ORR), duration of response, time to response, progression free survival (PFS), overall survival (OS), disease control rate (DCR), oncogenic allelic burden, or a combination thereof of the subject. Determining the responsiveness of the subject can comprise determining if the subject has a partial response to the treatment, if the subject has a complete response to the treatment, if the subject has a stable disease (SD) status, or if the subject has a progressive disease (PD) status. In some embodiments, the method comprises starting an additional treatment to the subject if the subject is indicated as in cancer relapse. The additional treatment can be the same or different from the current or prior combination treatment.

Additional methods for assessing cancer status of the subject include determining ECOG status. As used herein, ECOG status refers to Eastern Cooperative Oncology Group (ECOG) Performance Status (Oken M, et al Toxicity and response criteria of the Eastern Cooperative Oncology Group. *Am J Clin Oncol* 1982; 5 (6): 649-655), as shown below: 0, Fully active, able to carry on all pre-disease performance without restriction; 1, Restricted in physically strenuous activity but ambulatory and able to carry out work of a light or sedentary nature, e.g., light house work, office work; 2, Ambulatory and capable of all selfcare but unable to carry out any work activities; up and about more than 50% of waking hours; 3, Capable of only limited selfcare; confined to bed or chair more than 50% of waking hours; 4, Completely disabled; cannot carry on any selfcare; totally confined to bed or chair; and 5, Dead.

As described herein, the patient can achieve complete response or partial response after treatment with the anti-angiogenics and the PLK1 inhibitor. In some embodiments, the patient achieves a complete response. In some embodiments, the patient achieves a partial response. In some embodiments, the patient did not receive any prior anti-angiogenics treatment.

Disclosed herein include methods, compositions, kits, and systems for predicting/determining clinical outcome for a combination treatment of cancer of the present disclosure, monitoring of the combination treatment, predicting/determining responsiveness of a subject to the combination treatment, determining the status of the cancer in a subject, and improving combination treatment outcome. The methods, compositions, kits and systems can be used to guide the combination treatment, provide combination treatment recommendations, reduce or avoid unnecessary ineffective combination treatment for patients. In some embodiments, the combination treatment disclosed herein can improve oncogenic allelic burden in a subject. As used herein, “allelic burden” can refer to the ratio between mutant (e.g., oncogenic) and wild-type alleles in clinical samples employed for genotyping. In some embodiments, the sample can comprise circulating tumor DNA (ctDNA). ctDNA can be analyzed to predict/determine clinical outcome for cancer treatment, monitor cancer treatment, predict/determine responsiveness of a subject to a cancer treatment, determine cancer status in a subject, improve cancer treatment outcome, guide cancer treatment, provide treatment recommendations, and/or to reduce or avoid ineffective cancer treatment. Such analysis of ctDNA has been described in WO2021146322, the content of which is incorporated herein by reference in its entirety.

A method of determining responsiveness of a subject to a combination treatment comprising an anti-angiogenics and a PLK1 inhibitor of the disclosure can comprise, for example, analyzing ctDNA of a subject with cancer, wherein the subject is undergoing a treatment and/or has received the combination treatment, thereby determining the responsiveness of the subject to the combination treatment. In some embodiments, determining the responsiveness of the subject comprises determining if the subject is a responder of the treatment, if the subject is or is going to be in CR, or if the subject is or is going to be in partial remission (PR). For example, analyzing ctDNA can comprise detecting variant allele frequency in the ctDNA in a first sample obtained from the subject at a first time point, detecting variant allele frequency in the ctDNA obtained from the subject at one or more additional time points in one or more additional samples, and determining the difference of the variant allele frequency in ctDNA between the first and at least one of the one or more additional samples, a decrease in the variant allele frequency in at least one of the additional samples relative to the first sample indicates the subject as responsive to the cancer treatment.

In some embodiments, the first time point is prior or immediately prior to the combination treatment, and at least one of the one or more additional time points are at the end of or after at least a cycle of the combination treatment. In some embodiments, the cycle of the combination treatment is the first cycle of the combination treatment. In some embodiments, the first time point is prior or immediately prior to a first cycle of the combination treatment, and the one or more additional time points are at the end of or after a second cycle of the combination treatment.

In some embodiments, the first cycle of the combination treatment is immediately prior to the second cycle of the combination treatment. In some embodiments, the method comprises continuing the combination treatment to the subject if the subject is indicated as responsive to the combination treatment. In some embodiments, the method comprises discontinuing the combination treatment to the subject and/or starting a different combination treatment to the subject if the subject is not indicated as responsive to the combination treatment.

Disclosed herein include methods of determining cancer status of a subject, comprising analyzing ctDNA of a subject, thereby determining cancer status of the subject. The subject can be a subject undergoing a current combination treatment comprising an anti-angiogenics and a PLK1 inhibitor of the present disclosure, a subject that has received a prior combination treatment of the present disclosure, and/or a subject that is in remission for the cancer. The subject in remission for cancer can be in complete remission (CR), or in partial remission (PR).

In some embodiments, analyzing the ctDNA comprises detecting variant allele frequency in the ctDNA. In some embodiments, analyzing the ctDNA comprises detecting variant allele frequency in the ctDNA obtained from the subject at a first time point in a first sample, detecting variant allele frequency in the ctDNA obtained from the subject at one or more additional time points in one or more additional samples, and determining the difference of the variant allele frequency in ctDNA between the first and at least one of the one or more additional samples, an increase in the variant allele frequency at the additional sample(s) relative to the first sample indicates that the subject is at risk of cancer relapse or is in cancer relapse.

In some embodiments, the first time point is prior or immediately prior to the combination treatment, and the one or more additional time points are at the end of or after at least a cycle of the combination treatment, optionally the cycle of the combination treatment is the first cycle of the combination treatment. In some embodiments, the first time point is prior or immediately prior to a first cycle of the combination treatment, and the one or more additional time points are at the end of or after a second cycle of the combination treatment, optionally the first cycle of the combination treatment is immediately prior to the second cycle of the combination treatment.

In some embodiments, the method comprises starting an additional treatment to the subject if the subject is indicated as in cancer relapse. The additional treatment can be the same or different from the current or prior combination treatment.

The variant allele frequency in ctDNA can be determined, for example, by total mutation count in the ctDNA in each of the first sample and one or more additional samples, or by the mean variant allele frequency in each of the first sample and one or more additional samples. In some embodiments, the variant allele frequency is mutant allelic frequency (MAF) for a driver mutation of the cancer (e.g., metastatic colorectal cancer, metastatic bladder cancer, metastatic breast cancer, metastatic kidney cancer, metastatic lung cancer, metastatic ovarian cancer, metastatic pancreatic cancer, metastatic prostate cancer, metastatic stomach cancer, metastatic thyroid cancer, metastatic uterine cancer, metastatic renal cancer, metastatic cervical cancer, metastatic recurrent glioblastoma, or a combination thereof). In some embodiments, the variant allele frequency is MAF for one or more driver mutations of the cancer (e.g., metastatic colorectal cancer, metastatic bladder cancer, metastatic breast cancer, metastatic kidney cancer, metastatic lung cancer, metastatic ovarian cancer, metastatic pancreatic cancer, metastatic prostate cancer, metastatic stomach cancer, metastatic thyroid cancer, metastatic uterine cancer, metastatic renal cancer, metastatic cervical cancer, metastatic recurrent glioblastoma, or a combination thereof). In some embodiments, $\mathrm{Log}_2(C_1/C_0)$<a MAF threshold indicates a decrease in ctDNA MAF $C_0$ is ctDNA MAF in the first sample and $C_1$ is ctDNA MAF in one of the additional samples. In some embodiments, the MAF threshold is, or is about, 0.01 to −0.10. In some embodiments, the MAF threshold is, or is about, 0.06. In some embodiments, the MAF threshold is, or is about, 0.05.

In some embodiments, the first sample comprises ctDNA from the subject before treatment, and the one of additional samples comprises ctDNA from the subject after treatment.

The driver mutation can be, or can comprise, a mutation in one of the below 75 genes ABL1, ANKRD26, ASXL1, ATRX, BCOR, BCORL1, BRAF, BTK, CALR, CBL, CBLB, CBLC, CCND2, CDC25C, CDKN2A, CEBPA, CSF3R, CUX1, CXCR4, DCK, DDX41, DHX15, DNMT3A, ETNK1, ETV6, EZH2, FBXW7, FLT3, GATA1, GATA2, GNAS, HRAS, IDH1, IDH2, IKZF1, JAK2, JAK3, KDM6A, KIT, KMT2A, KRAS, LUC7L2, MAP2K1, MPL, MYC, MYD88, NF1, NOTCH1, NPM1, NRAS, PDGFRA, PHF6, PPMID, PTEN, PTPN11, RAD21, RBBP6, RPS14, RUNX1, SETBP1, SF3B1, SH2B3, SLC29A1, SMC1A, SMC3, SRSF2, STAG2, STAT3, TET2, TP53, U2AF1, U2AF2, WT1, XPO1, and ZRSR2. In some embodiments, at least one of the one or more the driver mutations is a mutation in in the 75 genes. In some embodiments, one or more the driver mutations are mutations in the 75 genes. The driver mutation or at least one of the one or more driver mutations can be in a gene selected from TP53, ASXL1, DNMT3A, NRAS, SRSF2, TET2, SF3B1, FLT3, FLT3 ITD, IDH2, NPM1, RUNX1, CDKN2A, KRAS, STAG2, CALR, CBL, CSF3R, DDX41, GATA2, JAK2, PHF6, and SETBP1. In some embodiments, the driver mutation or at least one of the one or more driver mutations is in a gene selected from the group consisting of DNMT3A, TET2, NPM1, SRSF2, NRAS, CDKN2A, SF3B1, FLT3, ASXL1, SRSF2, IDH2, NRAS, and SF3B1. In some embodiments, the method further comprises determining variant allele frequency in one or more of the ctDNA, PBMCs and BMMCs of the subject.

The ctDNA can be analyzed using, for example, polymerase chain reaction (PCR), next generation sequencing (NGS), and/or droplet digital PCR (ddPCR). The sample disclosed herein can be derived from, for example, whole blood of the subject, plasma of the subject, serum of the subject, or a combination thereof. In some embodiments, the ctDNA is from whole blood of the subject, plasma of the subject, serum of the subject, or a combination thereof.

In some embodiments, the method comprises analyzing ctDNA of the subject before the treatment. In some embodiments, the treatment comprises one or more cycles, and the ctDNA is analyzed before, during and after each cycle of the treatment. Each cycle of treatment can be at least 21 days. In some embodiments, each cycle of treatment is from about 21 days to about 28 days. In some embodiments, the subject is human.

Disclosed herein include methods of improving treatment outcome for the cancer. The method can comprise: detecting variant allele frequency in ctDNA obtained from a subject at a first time point in a first sample before the subject undergoes a combination treatment comprising an anti-angiogenics and a PLK1 inhibitor of the present disclosure; detecting variant allele frequency in ctDNA obtained from the subject at one or more additional time points in one or more additional samples after the subject undergoes the combination treatment; determining the difference of the variant allele frequency in ctDNA between the first and at least one of the one or more additional samples, a decrease in the oncogenic allelic burden and/or variant allele frequency in at least one of the additional samples relative to the first sample indicates the subject as responsive to the combination treatment; and continuing the combination treatment to the subject if the subject is indicated as responsive to the combination treatment, or discontinuing the combination treatment to the subject and/or starting a different cancer treatment to the subject if the subject is not indicated as responsive to the combination treatment.

Also disclosed herein include methods of treating cancer. The method can comprise: administering a combination treatment comprising an anti-angiogenics and a PLK1 inhibitor of the present disclosure to a subject in need thereof; determining a decrease, relative to an oncogenic allelic burden and/or variant allele frequency in a first sample of the subject obtained at a first time point before the subject receives the combination treatment, in a variant allele frequency in a second sample of the subject obtained at a second time point after the subject receives the combination treatment; and continuing with the combination treatment. In some embodiments, the subject is a subject newly diagnosed with cancer, for example a subject that has not received any prior cancer treatment before the combination treatment. In some embodiments, the subject has received prior cancer treatment and was in remission for the cancer, for example a subject in complete remission (CR), or in partial remission (PR) after receiving the prior combination treatment. In some embodiments, the prior treatment does not comprise the use of an anti-angiogenics, a PLK1 inhibitor, or both.

The first time point can be, for example, prior or immediately prior to the combination treatment. The at least one of the one or more additional time points can be, for example, at the end of or after at least a cycle of the combination treatment. In some embodiments, the cycle of the combination treatment is the first cycle of the combination treatment. In some embodiments, the first time point is prior or immediately prior to a first cycle of the combination treatment, and the one or more additional time points are at the end of or after a second cycle of the combination treatment. In some embodiments, the first cycle of the combination treatment is immediately prior to the second cycle of the combination treatment.

The variant allele frequency in ctDNA can be determined, for example, by total mutation count in the ctDNA in each of the first sample and one or more additional samples, and/or by the mean variant allele frequency in each of the first sample and one or more additional samples. In some embodiments, the variant allele frequency is mutant allelic frequency (MAF) for a driver mutation of the cancer (e.g., metastatic colorectal cancer, metastatic bladder cancer, metastatic breast cancer, metastatic kidney cancer, metastatic lung cancer, metastatic ovarian cancer, metastatic pancreatic cancer, metastatic prostate cancer, metastatic stomach cancer, metastatic thyroid cancer, metastatic uterine cancer, metastatic renal cancer, metastatic cervical cancer, metastatic recurrent glioblastoma, or a combination thereof). In some embodiments, the variant allele frequency is MAF for one or more driver mutations of the cancer (e.g., metastatic colorectal cancer, metastatic bladder cancer, metastatic breast cancer, metastatic kidney cancer, metastatic lung cancer, metastatic ovarian cancer, metastatic pancreatic cancer, metastatic prostate cancer, metastatic stomach cancer, metastatic thyroid cancer, metastatic uterine cancer, metastatic renal cancer, metastatic cervical cancer, metastatic recurrent glioblastoma, or a combination thereof). In some embodiments, $Log_2(C_1/C_0)$<a MAF threshold indicates a decrease in ctDNA MAF $C_0$ is ctDNA MAF in the first sample and $C_1$ is ctDNA MAF in one of the additional samples. In some embodiments, the MAF threshold is-0.05.

The method can further comprise determining variant allele frequency in one or more of the ctDNA, PBMCs and BMMCs of the subject. The variant allele frequency in ctDNA can be detected, for example, using polymerase chain reaction (PCR) or next generation sequencing (NGS). In some embodiments, the variant allele frequency in ctDNA is detected using droplet digital PCR (ddPCR). At least one of the first sample, the one or more additional samples, and the second sample can be derived from whole blood of the subject, plasma of the subject, serum of the subject, or a combination thereof. In some embodiments, the ctDNA is from whole blood of the subject, plasma of the subject, serum of the subject, or a combination thereof.

In some embodiments, the subject whose ctDNA is analyzed is undergoing or will be undergoing treatment for the cancer. The method can comprise analyzing ctDNA of the subject before the treatment. The treatment can comprise one or more cycles, and the ctDNA is analyzed before, during and after one or more cycles of the treatment. For example, the ctDNA can be analyzed before, during and after two or more cycle of the treatment, three or more cycle of the treatment, or each cycle of the treatment. Each cycle of treatment can be at least 21 days, for example, 21 days, 22 days, 23 days, 24 days, 25 days, 26 days, 27 days, 28 days, 29 days, 30 days, or more, or a range between any two of these values. In some embodiments, each cycle of treatment is from about 21 days to about 28 days. In some embodiments, each cycle of treatment is from 21 days to 28 days. In some embodiments, the subject is human.

Compositions and Kits

Disclosed herein include compositions and kits for treating cancer. In some embodiments, the kit comprises: a Polo-like kinase 1 (PLK1) inhibitor; and a manual providing instructions for administrating the PLK1 inhibitor with an anti-angiogenics to a subject for treating a metastatic cancer, wherein the subject has not received any prior cancer treatment or wherein the subject has not received any prior treatment comprising inhibiting angiogenesis. In some embodiments, the kit comprises the anti-angiogenics. The cancer can be, for example, metastatic colorectal cancer, metastatic bladder cancer, metastatic breast cancer, metastatic kidney cancer, metastatic lung cancer, metastatic ovarian cancer, metastatic pancreatic cancer, metastatic prostate cancer, metastatic stomach cancer, metastatic thyroid cancer, metastatic uterine cancer, metastatic renal cancer, metastatic cervical cancer, metastatic recurrent glioblastoma or a combination thereof.

In some embodiments, the instructions comprise instructions for administrating the PLK1 inhibitor and the anti-angiogenics simultaneously. In some embodiments, the instructions comprise instructions for administrating the PLK1 inhibitor and the anti-angiogenics sequentially. In some embodiments, the instructions comprise instructions for administering of the PLK1 inhibitor orally. In some embodiments, the instructions comprise instructions for administrating the anti-angiogenics orally. In some embodiments, the instructions comprise instructions for administrating the anti-angiogenics intravenously.

The instructions can comprise instructions wherein the subject has not received any prior cancer treatment, e.g., any prior cancer treatment comprising administration of an angiogenesis inhibitor (e.g., bev).

The instructions can comprise instructions the subject has received at least one prior treatment for the cancer. In some embodiments, the prior treatment does not comprise the use of an anti-angiogenics, a PLK1 inhibitor, or both. In some embodiments, the instructions comprise instructions the subject was in remission for the cancer. In some embodiments, the subject in remission for cancer was in complete remission (CR), or in partial remission (PR).

In some embodiments, the instructions comprise instructions for administering each of the anti-angiogenics and the PLK1 inhibitor to the subject in a cycle of at least twice within a week. In some embodiments, the instructions comprise instructions for administering each of the anti-angiogenics and the PLK1 inhibitor to the subject in a cycle of at least five times within a week. In some embodiments, the instructions comprise instructions for administering the anti-angiogenics, the PLK1 inhibitor, or both are in a cycle of at least 7 days. In some embodiments, each cycle of treatment is at least about 21 days. In some embodiments, each cycle of treatment is from about 21 days to about 28 days, for example 28 days. In some embodiments, the instructions comprise instructions for administering the PLK1 inhibitor on at least four days in the cycle. In some embodiments, the instructions comprise instructions for not administering the PLK1 inhibitor on at least one day in the cycle. In some embodiments, the instructions comprise instructions for administrating the anti-angiogenics daily. In some embodiments, the instructions comprise instructions for administrating the anti-angiogenics and the PLK1 inhibitor for at least two cycles. The instructions can comprise instructions for administrating the anti-angiogenics daily, weekly, bi-weekly, every three weeks, every four weeks, or monthly.

The anti-angiogenics can be capable of inhibiting VEGF-A, VEGFR-1, VEGFR-2, VEGFR-3, EGFR, HER2, PDGFR family proteins, RAF, Kit (or c-Kit), FLT3, CSF-1R, RET, Abl, Itk, LcK, c-FMS, FGFR family proteins, c-Met, PIGF, TNF-α, IFNs, ILs, bFGF, mTOR, or any combination thereof. The anti-angiogenics (e.g., angiogenic inhibitor) can be Afatinib (Gilotrif®), Axitinib (Inlyta®), Bevacizumab (Avastin®), Cabozantinib (Cometriq®), Cetuximab (Erbitux®), Erlotinib (Tarceva®), Everolimus (Afinitor®), Gefitinib (Iressa®), Imatinib (Gleevec®), Lapatinib (Tykerb®), Lenalidomide (Revlimid®), Lenvatinib mesylate (Lenvima®), Necitumumab (Portrazza™), Neratinib (Nerlynx®), Panitumumab (Vectibix®), Pazopanib (Votrient®), Pertuzumab (Perjeta®), Ramucirumab (Cyramza®), Regorafenib (Stivarga®), Sorafenib (Nexavar®), Sunitinib (Sutent®), Thalidomide (Synovir, Thalomid®), Trastuzumab (Ontruzant®), Vandetanib (Caprelsa®), or Ziv-aflibercept (Zaltrap®).

The PLK1 inhibitor can be selective and/or specific for PLK1. In some embodiments, the PLK1 inhibitor is a dihydropteridinone, a pyridopyrimidine, a aminopyrimidine, a substituted thiazolidinone, a pteridine derivative, a dihydroimidazo[1,5-f]pteridine, a metasubstituted thiazolidinone, a benzyl styryl sulfone analogue, a stilbene derivative, or any combination thereof. In some embodiments, the PLK1 inhibitor is onvansertib, BI2536, Volasertib (BI6727), GSK461364, AZD1775, CYC140, HMN-176, HMN-214, rigosertib (ON-01910), MLN0905, TKM-080301, TAK-960 or Ro3280. In some embodiments, the PLK1 inhibitor is onvansertib. In some embodiments, the anti-angiogenics is bevacizumab, and the PLK1 inhibitor is onvansertib. In some embodiments, the instructions comprise instructions for administering the PLK1 inhibitor at 12 $mg/m^2$-90 $mg/m^2$. In some embodiments, the instructions comprise instructions for administering the anti-angiogenics at 20 mg-1200 mg.

EXAMPLES

Some aspects of the embodiments discussed above are disclosed in further detail in the following examples, which are not in any way intended to limit the scope of the present disclosure.

Example 1

Clinical Trial of Onvansertib in Combination with Bevacizumab and FOLFIRI

This example describes the results (as of Jul. 25, 2022) of a Phase 1b/2 clinical trial (NCT03829410) for determining the safety and efficacy of onvansertib in combination with FOLFIRI and bevacizumab (which is the current standard of care for the second line treatment of patients whose disease has relapsed or progressed following first line treatment with oxaliplatin and fluoropyrimidine). Patients received the standard doses and schedule of FOLFIRI and bevacizumab ("bev") on Days 1 and 15 of a 28-day treatment cycle, and onvansertib orally once daily on Days 1 through 5, and Days 15 through 19 of the 28-day cycle. Patients were scanned at baseline and every eight weeks on treatment for disease response assessment. The trial was conducted to show that onvansertib safely complements and improves the efficacy of the standard or care.

The three efficacy endpoints for the Phase 2 portion of the trial are: (1) the primary efficacy endpoint: the objective response rate (or ORR); (2) secondary endpoints: other measures of disease response, including progression free survival and duration of response; and (3) for one of the exploratory endpoints, we evaluated the correlation between changes in the KRAS mutation burden in circulating tumor DNA and radiographic disease response.

Table 1 shows the enrollment and patient characteristics for the study.

TABLE 1

Patient enrollment

| Number of Patients(N) | Phase 1b, Dose Level 0 Onvansertib 12 $mg/m^2$ | Phase 1b, Dose Level + 1 Onvansertib 15 $mg/m^2$ | Phase 1b, Dose Level + 2 Onvansertib 18 $mg/m^2$ | Phase 2 RP2D Onvansertib 15 $mg/m^2$ | Total Patients All Doses |
|---|---|---|---|---|---|
| Treated | 6 | 6 | 6 | 32 | 50 |
| In treatment | 0 | 0 | 0 | 3 | 3 |

RP2D, recommended phase 2 dose

TABLE 2

| Patient characteristics | |
|---|---|
| Total Patients N = 50 | Median n (%) |
| Liver metastasis | |
| None | 13 (26%) |
| Liver and other | 27 (54%) |
| Liver only | 10 (20%) |
| Number of metastatic organs | |
| 1 | 16 (32%) |
| ≥2 | 34 (68%) |
| Prior bevacizumab treatment | |
| Yes | 35 (70%) |
| No | 15 (30%) |

TABLE 3

| Strong, durable response achieved in patients | | |
|---|---|---|
| | All Doses | RP2D |
| Objective Response Rate* (CR + PR) | 35% (17/48) | 34% (12/35) |
| Disease Control Rate (CR + PR + SD) | 92% (44/48) | 94% (33/35) |
| Durability | | |
| Median Duration of Response | 11.7 months | 12.5 months |

Initial PRs up to eight months on treatment were observed. It was found that onvansertib in combination with FOLFIR-bev was well tolerated. Neutropenia is the most commonly reported TEAE, and over half of the events observed are Grade 3 or 4. Although it is part of standard FOLFIRI, the 5FU bolus is thought to add only to the toxicity of the regimen but not to the efficacy. Early in the Phase 1b portion of the trial, based on feedback from our investigators, we amended the protocol to permit discontinuation of the 5FU bolus from the treatment regimen if neutropenia of grade 2 or higher was observed. Discontinuation of the 5FU bolus, with or without the use of growth factors, has subsequently been shown to ameliorate the severity of neutropenia observed.

Figure 2:
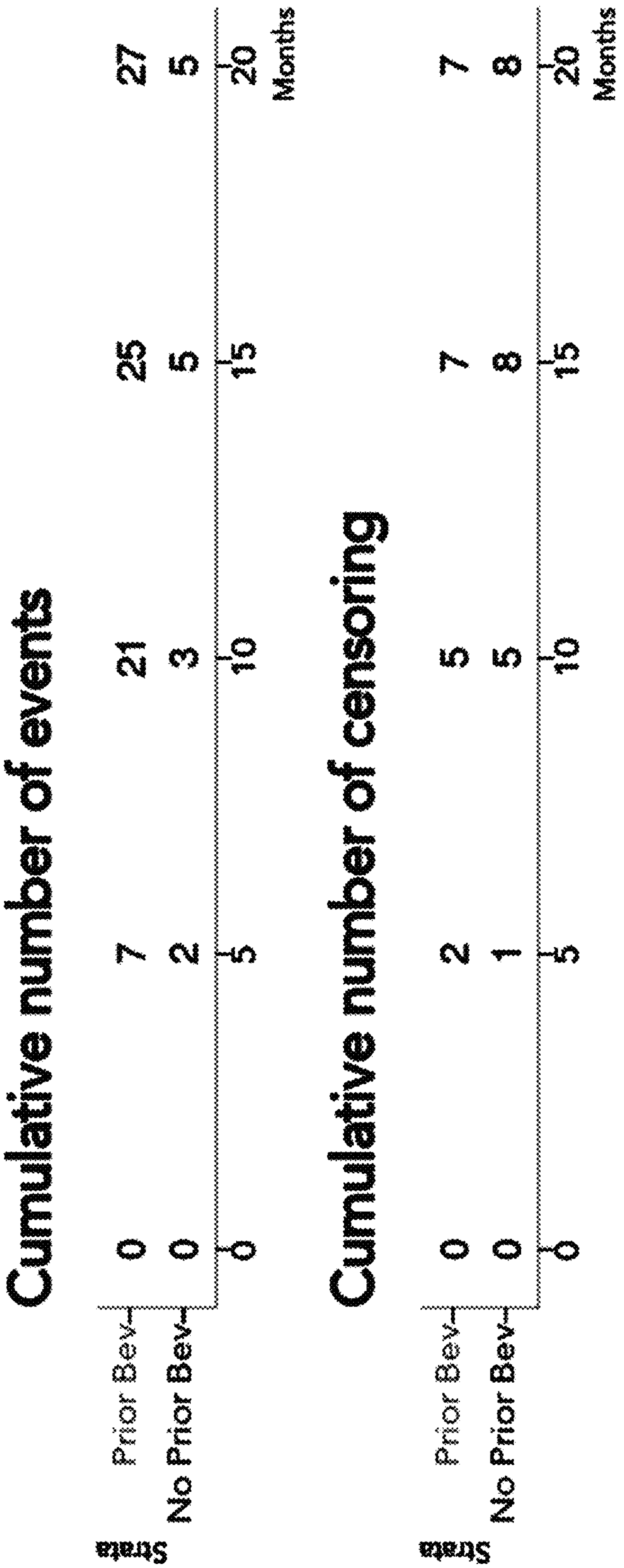
FIG. 2 depicts number of events and censoring (non-reporting) patients for the study described herein.

First line use of bev in prior clinical trials had minimal impact on the efficacy of second line use. In those prior trials (e.g., Hansen et al., Cancers 2021, 13, 1031; Tabernaro et al. Eur J Cancer, 2014, 50, 320-332; Bennouna et al., Lancet Oncol. 2013, 14, 29-37; Van Cutsem et al., J. Clin. Oncol. 2012, 30, 3499-3506; Tabenaro et al, Lancet Oncol 2015; 16:499-508; Beretta et al., Med Oncol (2013) 30:486; Moriwakij et al, Med Oncol (2012) 29:2842-2848), mPFS (mo) was 6.7 and 6.9 months and mOS (mo) was 12.5 and 13.9 months for patients that have received prior bev treatment ("prior bev") versus patients that didn't received prior bev treatment ("bev naïve") respectively. The conclusion from previous trials is that the mPFS and mOS are similar in 2nd line regardless of whether patients were bev naïve or had prior bev in 1st line. For ORR, there is an incremental increase of 12 to 20%. Surprisingly, it was found in the present trial (NCT03829410 "Onvansertib in Combination With FOLFIRI and Bevacizumab for Second Line Treatment of Metastatic Colorectal Cancer Patients With a Kras Mutation") that the "No Prior Bev" subset had a much greater than expected ORR and mPFS (See FIG. 1-FIG. 2). For ORR for 33 patients with prior bevacizumab treatment, there were 8/35 responders (22.9%) ORR (CI: 10.4%-40.1%). The ORR for 15 patients without prior bevacizumab was 9/13 responders (69.2%) ORR (CI: 38.6%-90.9%). Therefore, the ORR for patients with no prior anti-angiogenesis treatment was 2-fold greater than for those with prior anti-angiogenesis treatment, with an odds ratio of 0.14 (0.03-0.56, p=0.0049). PFS for patients with vs without prior bevacizumab also showed a surprising improvement for patients without prior bevacizumab treatment. In the present trial, the mPFS was 7.8 months for patients with prior bevacizumab and 13.5 months for patients without prior bevacizumab treatment (p=0.14) (FIG. 1).

TABLE 4

| Events | | | | | |
|---|---|---|---|---|---|
| | N | Events | Median | 0.95 LCL | 0.95 UCL |
| Prior Bev | 35 | 28 | 7.79 | 6.54 | 11.1 |
| No Prior Bev | 13 | 5 | 13.51 | 13.51 | NR |

Bev, Bevacizumab
LCL, Lower Control Limit
UCL, Upper Control Limit

Figure 3:
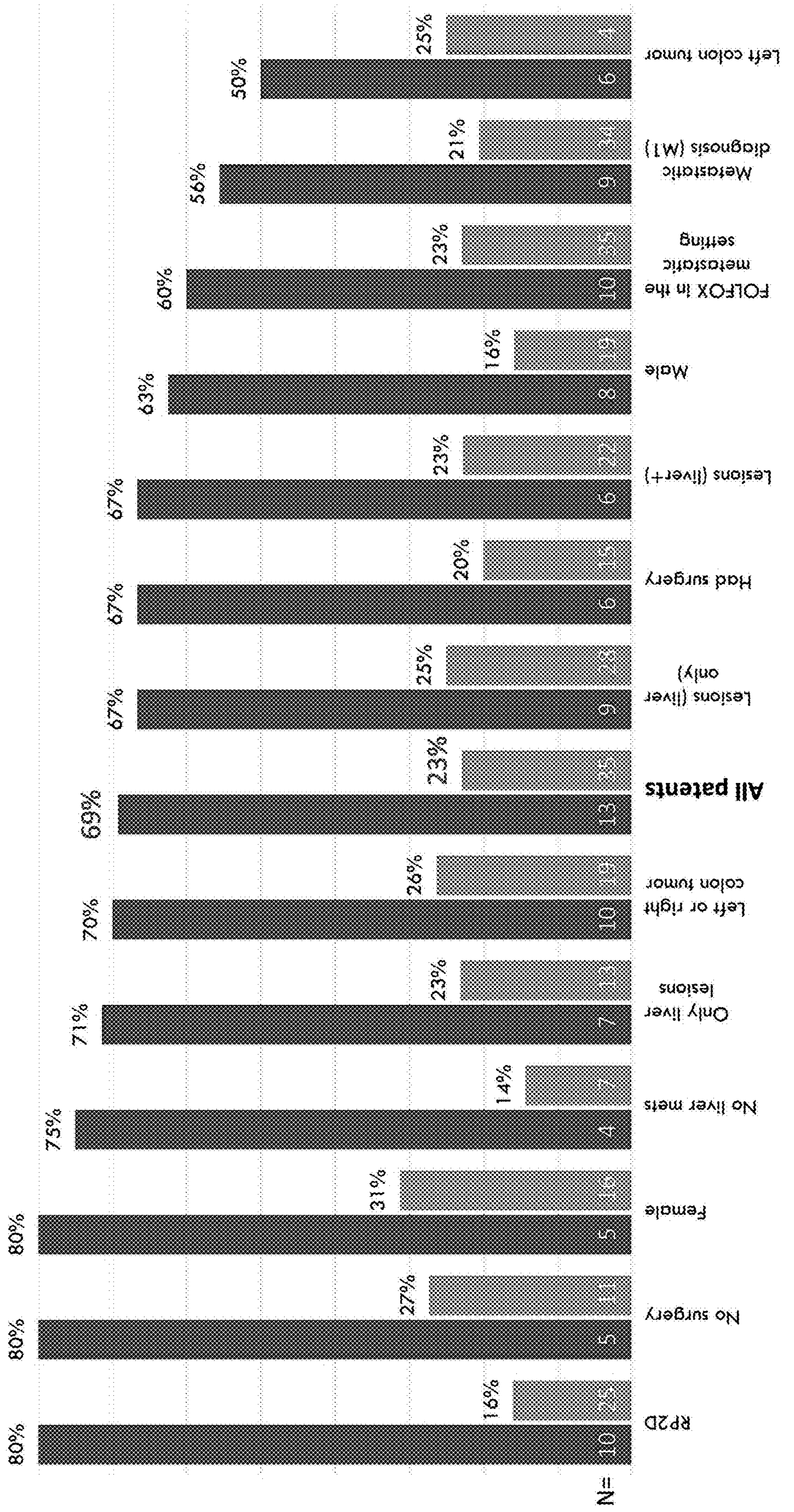
FIG. 3 depicts objective response rates for a cohort of patients treated using the methods and compositions provided herein, broken down by patients who had or had not received previous anti-angiogenics treatment. Numbers in boxes are the total number of patients in the indicated group.

It was found that ORR is consistently greater for bev naïve patients across characteristics. No single patient characteristic explains the observed ORR difference. As shown in FIG. 3 and Table 5, the lowest ORR for the No Prior Bev group was 50%, with the highest 80% in RP2D. ORR ranges from 14% to 31.3% depending on the variable for patients with prior bevacizumab treatment.

TABLE 5

| Observed ORR | | |
|---|---|---|
| | No Bev exposure in 1$^{st}$ line (naïve) | Bev exposure in 1$^{st}$ line (exposed) |
| Range of ORRs | 50-80% | 14-31% |

The results presented herein show a surprising improvement in multiple outcomes (e.g., ORR, PFS) for metastatic cancer patients treated with a combination of onvansertib and bevacizumab in patients without prior bev treatment. Without being bound by any particular theory, it is believed that there is a synergy between onvansertib and bevacizumab in a bev naïve setting.

Example 2

Therapeutic Benefits to Bev Naïve Patients

Figure 4B:
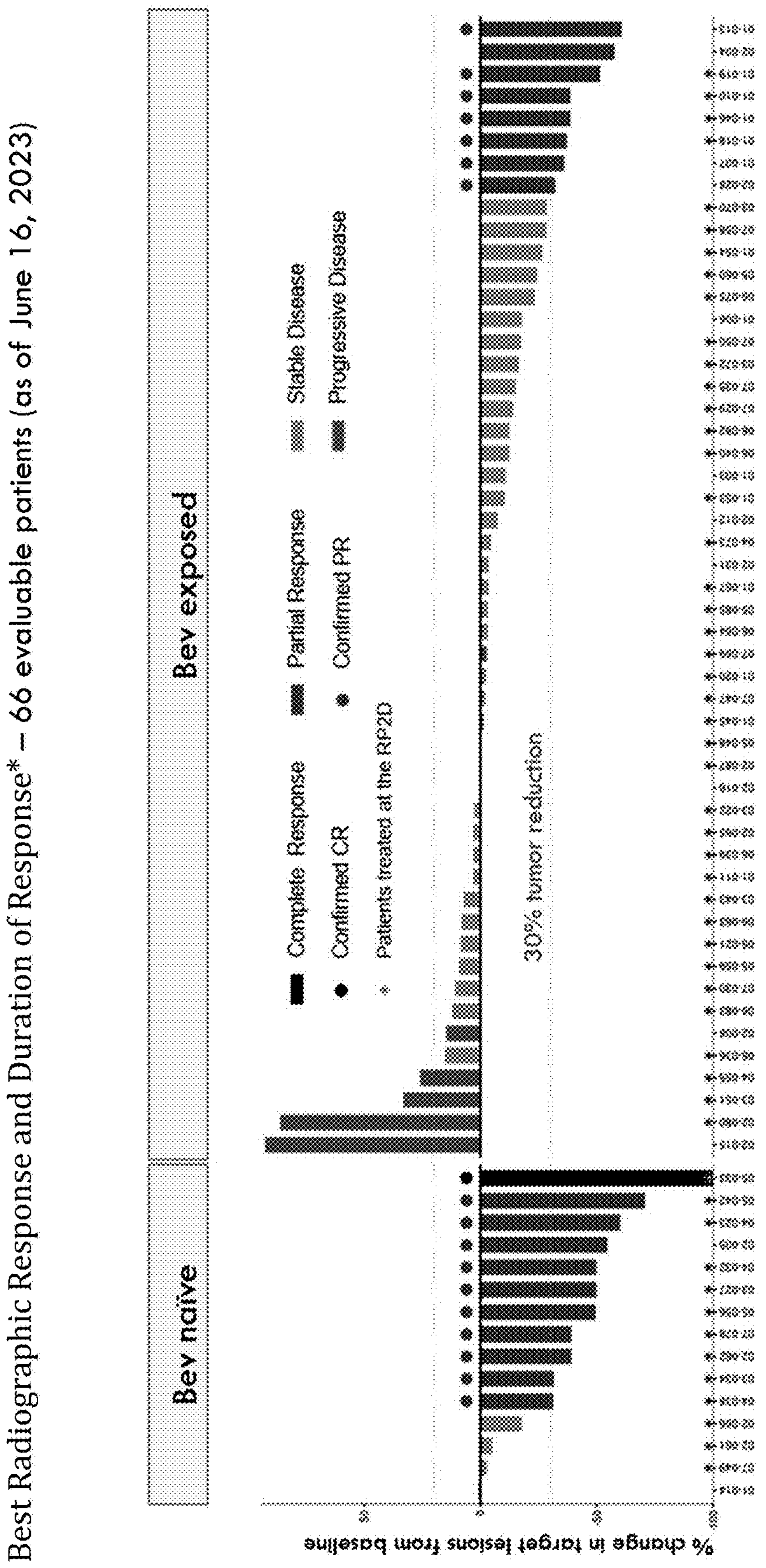
Figure 5A:
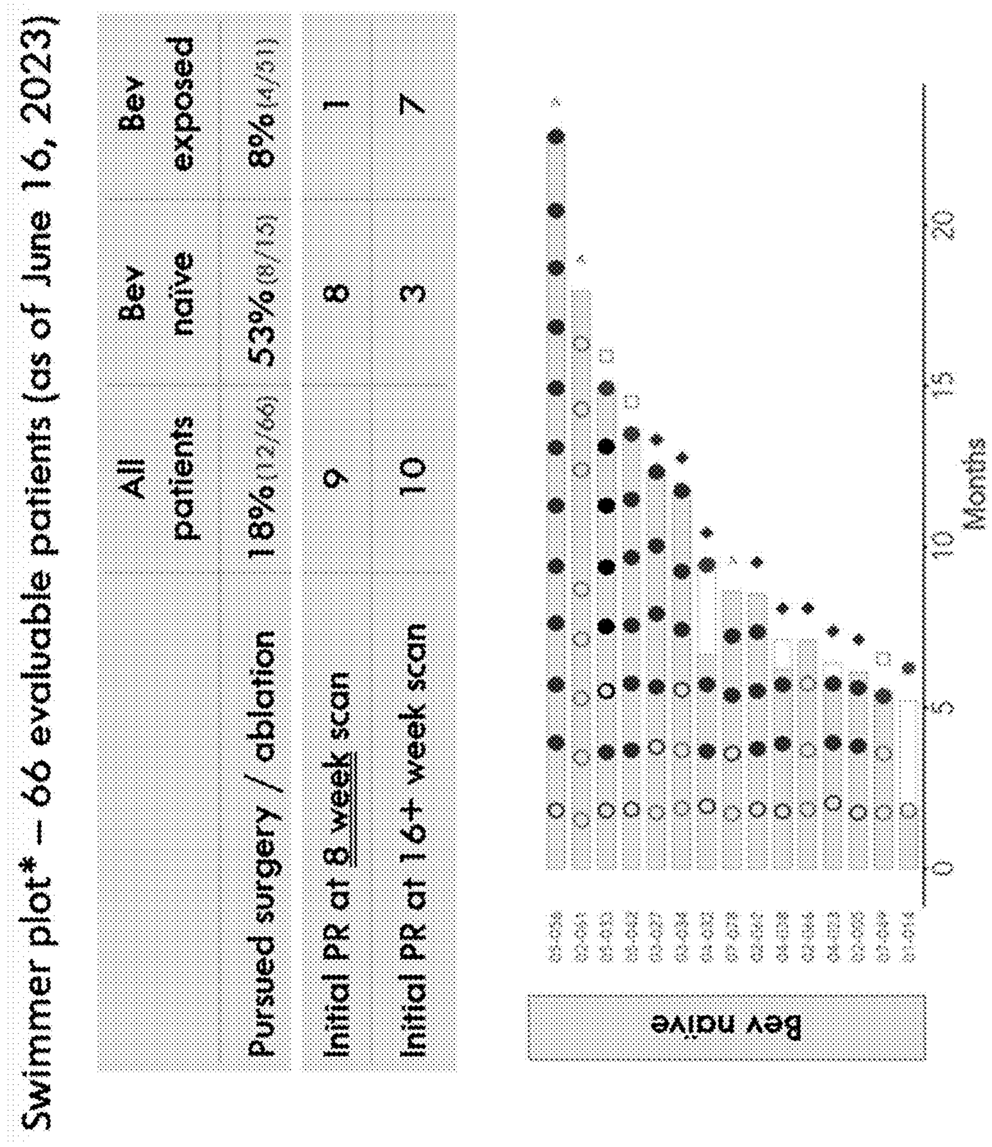
FIGS. 5A-5B are simmer plots showing responses of the 66 evaluable patients (as of Jun. 16, 2023). *Swimmer plot/table reflect interim data as of Jun. 16, 2023 from an ongoing trial and unlocked database. After external review of the tumor measurements completed May 12, 2023, it was determined that patients 02-028 and 04-038 were confirmed PRs.
Figure 5B:
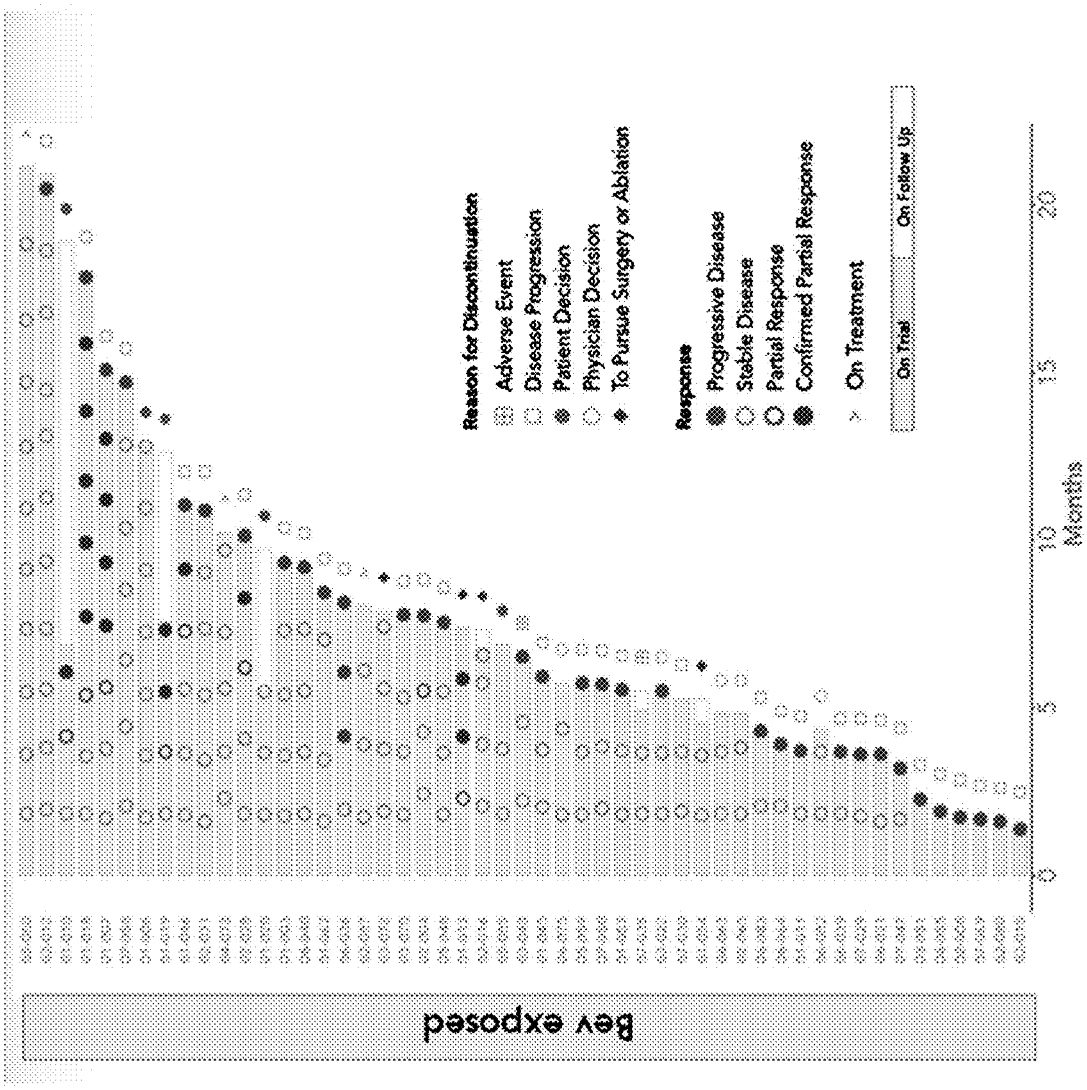

FIG. 4A depicts the Best Radiographic Response and Duration of Response for 66 evaluable patients (as of Jun. 16, 2023). FIGS. 4A-4B show that bev naïve patients achieved higher response rate with onvansertib in combination with FOLFIRI and bevacizumab (which is the current standard of care (SoC) for patients with metastatic colorectal cancer. In FIG. 4A, historical controls were derived from Bennouna et al., Lancet Oncol 2013; 14:29-37; Giessen et al., Acta Oncologica, 2015, 54:187-193; Cremolini et al., Lancet Oncol 2020, 21:497-507; Antoniotti et al., Correspondence Lancet Oncol June 2020. Giantonio et al., 2007, J Clin Oncol 25:1539-1544; Moriwaki et al., Med Oncol, 2012, 29:2842-2848; Beretta et al, Med Oncol 2013, 30:486. Also, Bev naïve patients experienced more durable responses (FIGS. 5A-5B**).

Figure 6:
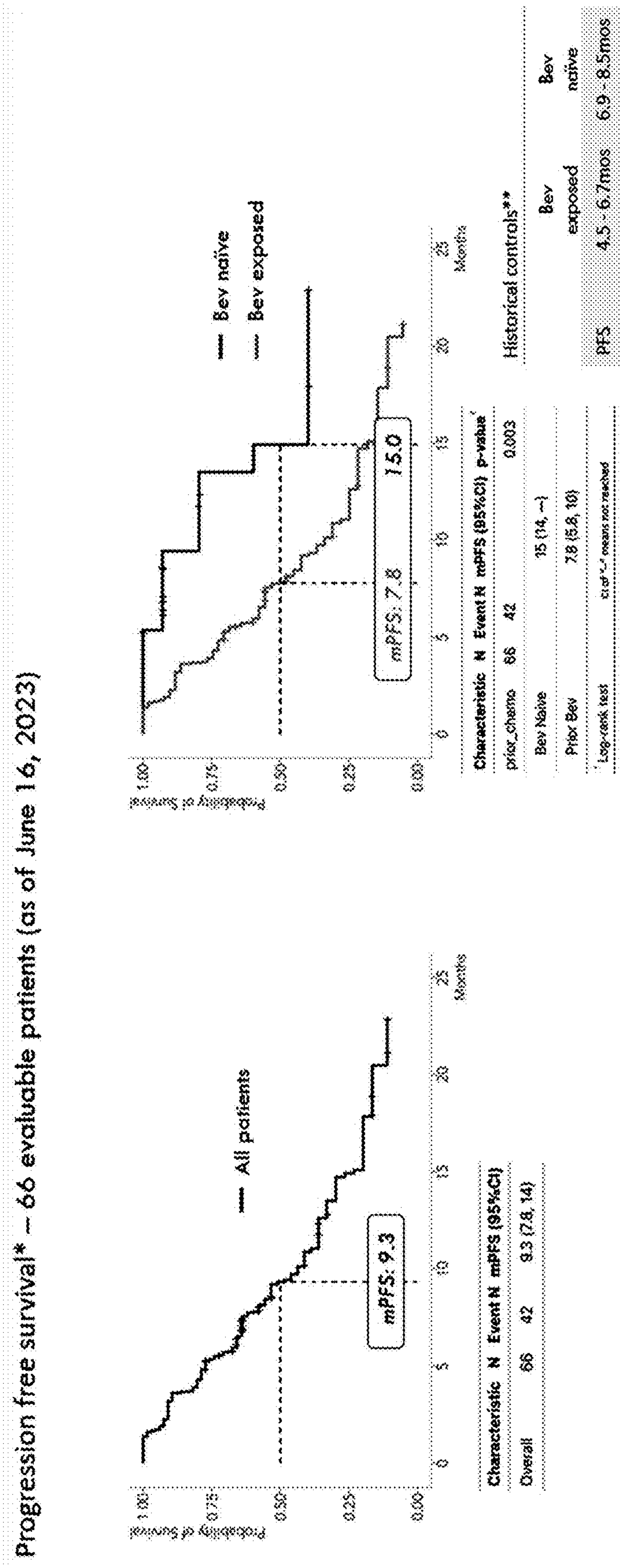
FIG. 6 depicts plots showing progression free survival of the 66 evaluable patients (as of Jun. 16, 2023). *Onvansertib mPFS are interim data as of Jun. 16, 2023 from an ongoing trial and unlocked database.

PFS for the patients under treatment was found to exceed historical controls for SoC, particularly in bev naïve patients. The progression free survival from 66 evaluable patients (as of Jun. 16, 2023) are shown in FIG. 6 (in FIG. 6, **historical controls were derived from Bennouna et al., Lancet Oncol 2013; 14:29-37; Giessen et al., Acta Oncologica, 2015, 54: 187-193; Cremolini et al., Lancet Oncol 2020, 21:497-507; Antoniotti et al., Correspondence Lancet Oncol June 2020. Giantonio et al., 2007, J Clin Oncol 25:1539-1544; Moriwaki et al., Med Oncol, 2012, 29:2842-2848; Beretta et al, Med Oncol 2013, 30:486.)

Figure 7:
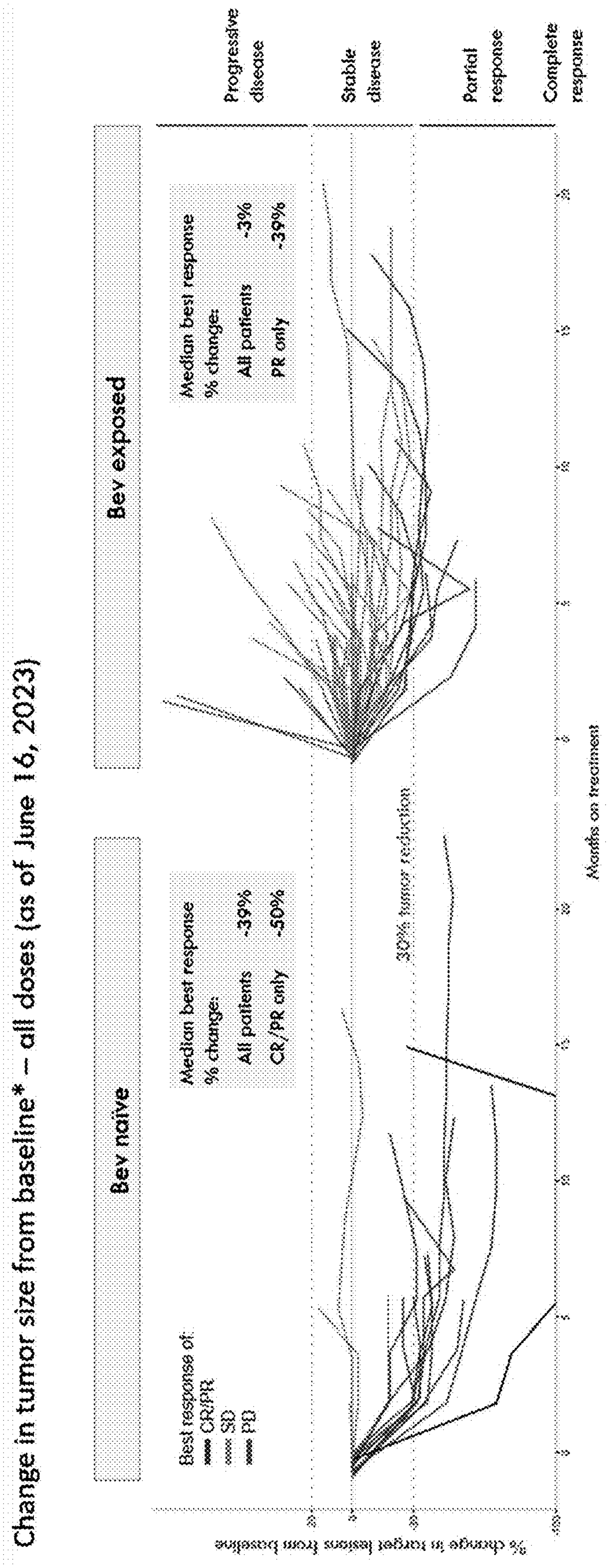
FIG. 7 shows plots showing changes in tumor size from baseline. *Spider plots reflect interim data as of Jun. 16, 2023 from an ongoing trial and unlocked database.

It was also observed that Bev naïve patients experienced deeper tumor regression. FIG. 7 shows change in tumor size from baseline*-all doses (as of Jun. 16, 2023).

Example 3

Figure 8:
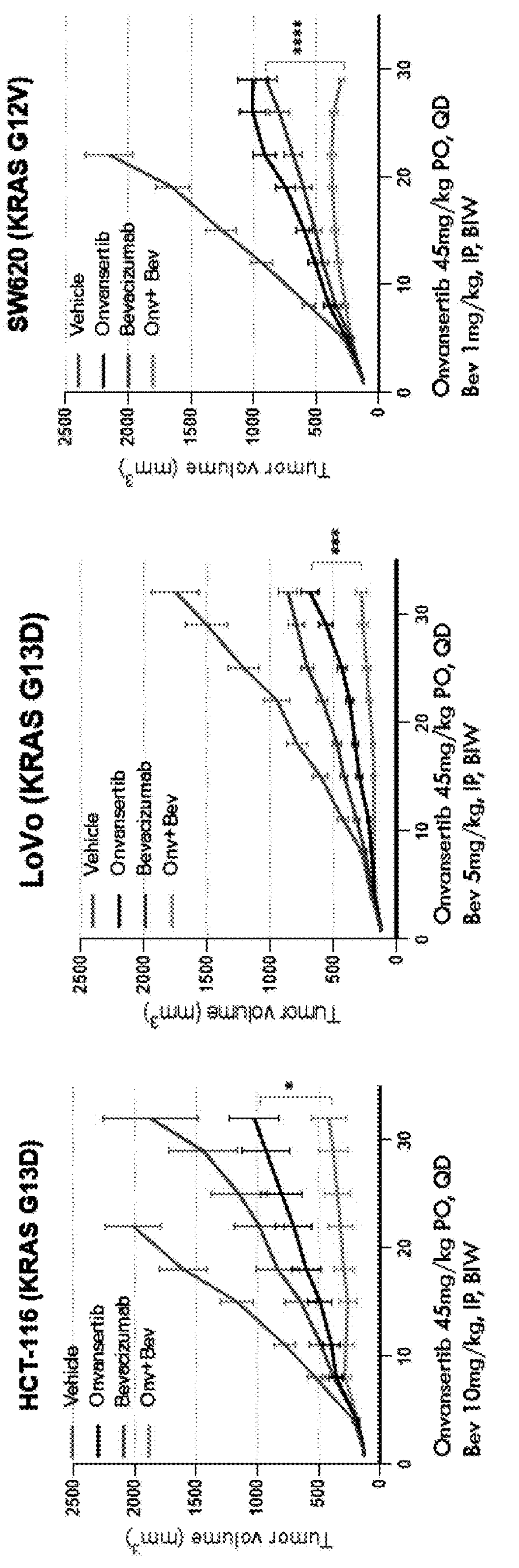
FIG. 8 shows changes in tumor volume in KRAS-mutant xenograft models when treated with vehicle, onvansertib, bevacizumab or the combination of onvansertib and bevacizumab. 8-9 mice/group. Mean±SEM are represented on graphs. An unpaired t-test was used to test the difference in tumor volume change on the last day of treatment between the combination treatment and the most effective control arm. *$p<0.05$, *$p<0.001$, **$p<0.0001$.
Figure 9:
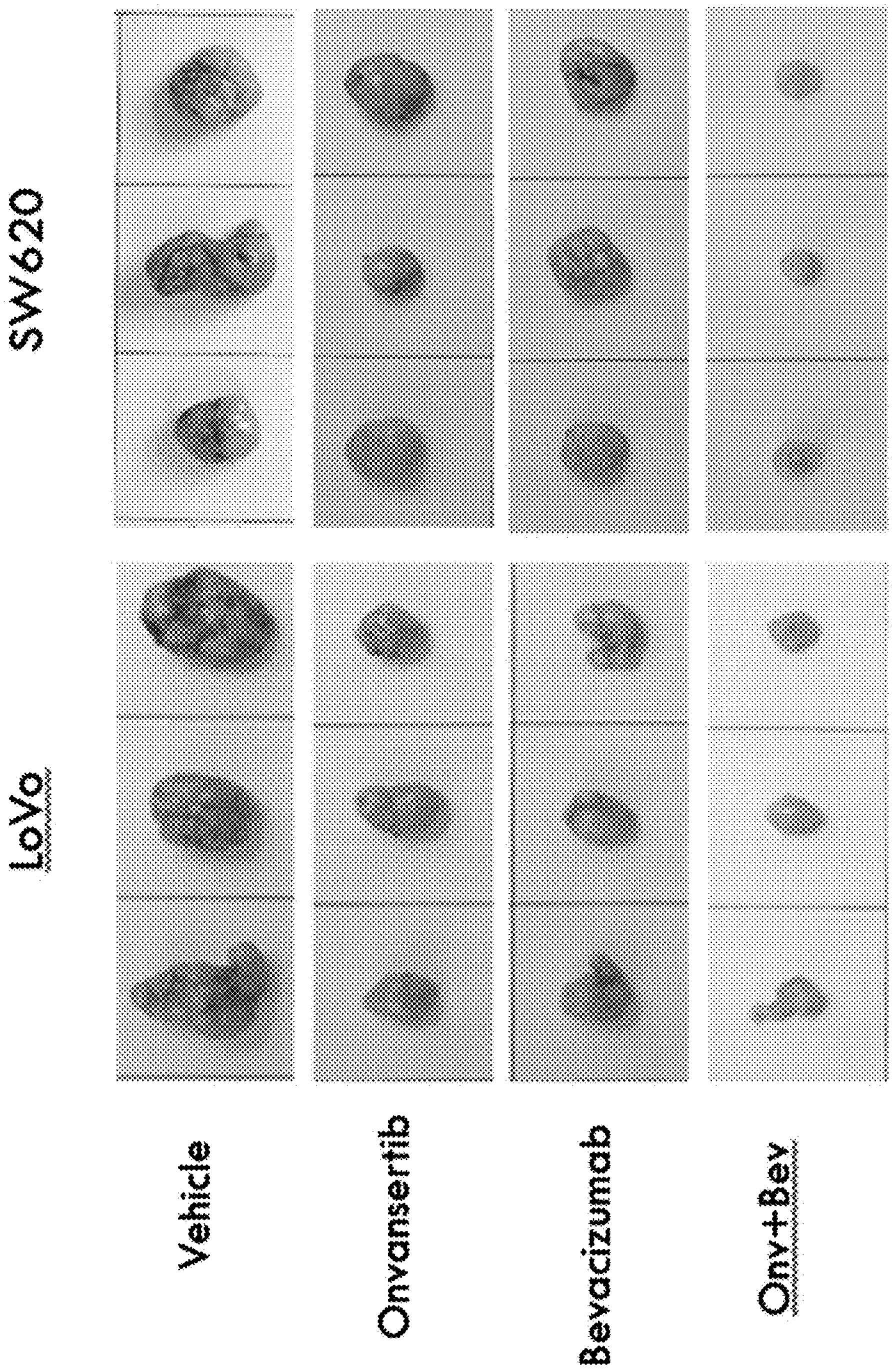
FIG. 9 shows changes in tumor vascularization in KRAS-mutant xenograft models when treated with vehicle, onvansertib, bevacizumab or the combination of onvansertib and bevacizumab.

Onvansertib in Combination with Bevacizumab is an Efficacious Combination in KRAS-Mutant CRC Xenograft Models Three KRAS-mutant xenograft models (HCT116, LoVo and SW620) were treated with vehicle, onvansertib, bevacizumab, or the combination of onvansertib and bevacizumab. As shown in FIG. 8, the combination of onvansertib and bevacizumab exhibited anti-tumor activity in the 3 models, including: (1) tumor stabilization was observed upon treatment with the combination; (2) the combination had significant superior anti-tumor activity compared to the single agents. FIG. 9 shows that the combination of onvansertib and bevacizumab reduces tumor vascularization, demonstrated by the observation that tumors from mice treated with the combination of onvansertib and bevacizumab appear smaller and pale (less vascularized).

Figure 10:
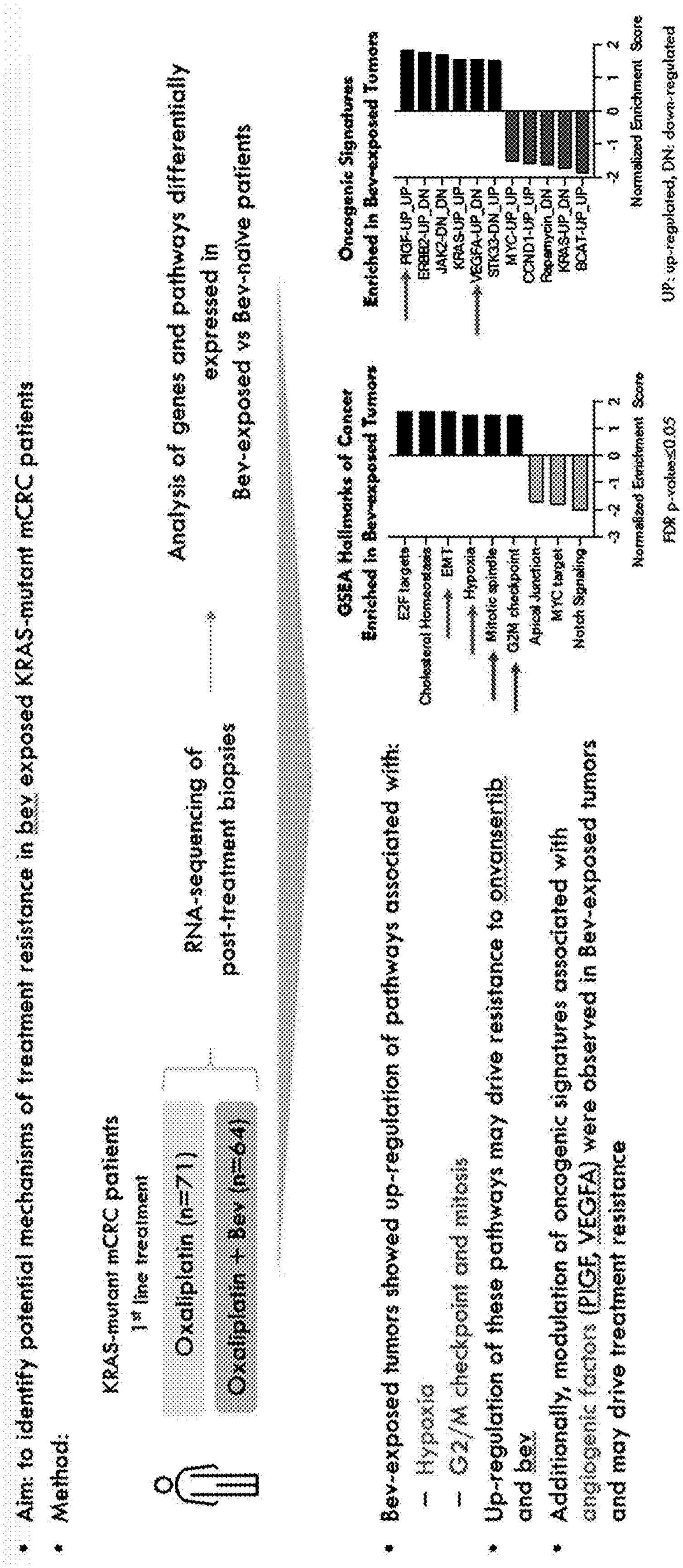
FIG. 10 shows a non-limiting method that can be used to identify potential mechanisms of treatment resistance in bev exposed KRAS-mutant mCRC patients.

Without being bound by any particular theory, it is believed that prior bev treatment modulates gene pathways that can confer resistance to bev and onvansertib. A non-limiting method shown in FIG. 10 can be used to identify potential mechanisms of treatment resistance in bev exposed KRAS-mutant mCRC patients.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms “a,” “an,” and “the” include plural references unless the context clearly dictates otherwise. Any reference to “or” herein is intended to encompass “and/or” unless otherwise stated.

It will be understood by those within the art that, in general, terms used herein, and especially in the appended claims (e.g., bodies of the appended claims) are generally intended as “open” terms (e.g., the term “including” should be interpreted as “including but not limited to,” the term “having” should be interpreted as “having at least,” the term “includes” should be interpreted as “includes but is not limited to,” etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases “at least one” and “one or more” to introduce claim recitations. However, the use of such phrases should not be construed to imply that the introduction of a claim recitation by the indefinite articles “a” or “an” limits any particular claim containing such introduced claim recitation to embodiments containing only one such recitation, even when the same claim includes the introductory phrases “one or more” or “at least one” and indefinite articles such as “a” or “an” (e.g., “a” and/or “an” should be interpreted to mean “at least one” or “one or more”); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of “two recitations,” without other modifiers, means at least two recitations, or two or more recitations). Furthermore, in those instances where a convention analogous to “at least one of A, B, and C, etc.” is used, in general such a construction is intended in the sense one having skill in the art would understand the convention (e.g., “a system having at least one of A, B, and C” would include but not be limited to systems that have A alone, B alone, C alone, A and B together, A and C together, B and C together, and/or A, B, and C together, etc.). In those instances where a convention analogous to “at least one of A, B, or C, etc.” is used, in general such a construction is intended in the sense one having skill in the art would understand the convention (e.g., “a system having at least one of A, B, or C” would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as “up to,” “at least,” “greater than,” “less than,” and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of treating a subject having a metastatic colorectal cancer, comprising:

administering to the subject an effective amount of onvansertib and bevacizumab if the patient has not received any prior treatment with bevacizumab, thereby reducing or inhibiting progression of the metastatic colorectal cancer, wherein onvansertib is administered multiple doses and bevacizumab is administered multiple doses during a treatment cycle.

2. The method of claim 1, wherein the metastatic colorectal cancer is KRAS-mutated metastatic colorectal cancer.

3. The method of claim 1, wherein the treatment with onvansertib and bevacizumab comprises at least two cycles of the administration of onvansertib and bevacizumab and wherein onvansertib is administered on at least four days in the cycle and bevacizumab is administered weekly or biweekly.

4. The method of claim 1, further comprising determining the responsiveness of the subject to the onvansertib and bevacizumab treatment.

5. The method of claim 4, wherein determining the responsiveness of the subject to the onvansertib and bevacizumab treatment comprises determining objective response rate (ORR), duration of response, time to response, progression free survival (PFS), overall survival (OS), disease control rate (DCR), oncogenic allelic burden, or a combination thereof of the subjects.

6. The method of claim 1, further comprising determining cancer status of the subject.

7. The method of claim 1, wherein onvansertib and bevacizumab are administered simultaneously or sequentially.

8. The method of claim 1, wherein the administration of onvansertib is oral administration, and the administration of bevacizumab is intravenous administration or oral administration.

9. The method of claim 1, further comprising administering to the subject one or more cancer therapeutics or therapies.

10. The method of claim 9, wherein the one or more cancer therapeutics or therapies comprise FOLFIRI, abiraterone, FOLFOX, an anti-EGFR agent, a KRAS directed inhibitor, gemcitabine, abraxane, nanoliposomal irinotecan, 5-FU, or a combination thereof.

11. The method of claim 1, wherein onvansertib is administered at 12 $mg/m^2$-90 $mg/m^2$.

12. The method of claim 1, wherein bevacizumab is administered at about 1 mg/kg-20 mg/kg.

13. The method of claim 1, wherein onvansertib and bevacizumab are administered to the subject in combination with FOLFIRI.

14. The method of claim 1, wherein onvansertib and bevacizumab are administered to the subject in combination with FOLFOX.

15. The method of claim 1, wherein onvansertib and bevacizumab synergistically improves the ORR and/or the PFS in the subject.

16. The method of claim 1, wherein the subject achieves about 2-fold, 3-fold, 4-fold or 5-fold higher ORR compared to subjects who have received prior bevacizumab treatment.

17. The method of claim 1, wherein the subject achieves about 2-fold higher PFS compared to subjects who have received prior bevacizumab treatment.

18. The method of claim 1, wherein the subject is human.

19. The method of claim 1, wherein the subject has not received any prior chemotherapy.

20. The method of claim 19, wherein the prior chemotherapy comprises a treatment using FOLFIRI, abiraterone, FOLFOX, an anti-EGFR agent, a KRAS directed inhibitor, gemcitabine, abraxane, nanoliposomal irinotecan, 5-FU, FOLFIRINOX, FOLFOXIRI, or a combination thereof.

* * * * *